[12] United States Patent
Minoda et al.

(10) Patent No.: US 10,685,579 B2
(45) Date of Patent: Jun. 16, 2020

(54) LEARNING SYSTEM, LEARNING METHOD, STORAGE MEDIUM, AND APPARATUS

(71) Applicant: Panasonic Intellectual Property Management Co., Ltd., Osaka (JP)

(72) Inventors: Yuki Minoda, Tokyo (JP); Koji Morikawa, Tokyo (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 540 days.

(21) Appl. No.: 15/581,046

(22) Filed: Apr. 28, 2017

(65) Prior Publication Data

US 2017/0330475 A1 Nov. 16, 2017

(30) Foreign Application Priority Data

May 13, 2016 (JP) ................................. 2016-097314

(51) Int. Cl.
*G09B 7/08* (2006.01)
*G09B 7/02* (2006.01)
*A61B 5/0484* (2006.01)
*A61B 5/0476* (2006.01)
*G09B 7/06* (2006.01)

(52) U.S. Cl.
CPC .............. *G09B 7/08* (2013.01); *A61B 5/0476* (2013.01); *A61B 5/0484* (2013.01); *G09B 7/02* (2013.01); *G09B 7/06* (2013.01); *A61B 2503/12* (2013.01)

(58) Field of Classification Search
None
See application file for complete search history.

(56) References Cited

U.S. PATENT DOCUMENTS

| 2002/0103429 | A1* | 8/2002 | deCharms | A61B 5/055 600/410 |
| 2002/0152187 | A1* | 10/2002 | Chien | G09B 7/02 706/60 |
| 2003/0129574 | A1* | 7/2003 | Ferriol | G09B 5/00 434/362 |
| 2007/0231780 | A1* | 10/2007 | Shulman | G09B 7/08 434/350 |
| 2009/0142743 | A1 | 6/2009 | Adachi et al. | |

FOREIGN PATENT DOCUMENTS

| JP | 10-078743 | 3/1998 |
| WO | 2007/148469 | 12/2007 |

* cited by examiner

*Primary Examiner* — Bruk A Gebremichael
(74) *Attorney, Agent, or Firm* — Wenderoth, Lind & Ponack, L.L.P.

(57) ABSTRACT

A learning system includes an output unit that outputs a first problem and a display message prompting a user to take a break, an acquisition unit that acquires an answer to the first problem from the user, an electroencephalogram measurement unit that measures an electroencephalogram of the user, and a control unit. The control unit determines whether first motivation is present on the basis of a first event-related potential included in the electroencephalogram and starting from a timing at which the first problem is output, determines whether second motivation of the user is present on the basis of a second event-related potential included in the electroencephalogram and starting from a timing at which the answer is acquired, and instructs the output unit to output a display message prompting the user to take a break if the first motivation is not present and the second motivations is not present.

23 Claims, 17 Drawing Sheets

|  | SECOND MOTIVATION | |
|---|---|---|
| FIRST MOTIVATION | PRESENT | NOT PRESENT |
| PRESENT | STATE 1 | STATE 1 |
| NOT PRESENT | STATE 1 | STATE 2 |

LEARNING SYSTEM, LEARNING METHOD, STORAGE MEDIUM, AND APPARATUS

BACKGROUND

1. Technical Field

The present disclosure relates to a learning system, a learning method, a storage medium, and an apparatus that present a problem and acquire an answer to the problem from a user.

2. Description of the Related Art

Japanese Unexamined Patent Application Publication No. 10-78743 describes a learning control apparatus that measures biometric information, such as the skin impedance of a learner, and presents learning information selected on the basis of the biometric information.

Japanese Patent No. 4189440 describes a service providing system. The service providing system described in Japanese Patent No. 4189440 includes an output unit, a signal detection unit, and a determination unit. The output unit presents a problem to the user and, thereafter, presents a plurality of options one after another as the candidate answers to the problem. The signal detection unit measures the event-related potential in the user's electroencephalogram. The determination unit determines whether the user considers each of the options as a correct answer on the basis of the event-related potential during a predetermined time period after presenting the option.

SUMMARY

However, in Japanese Unexamined Patent Application Publication No. 10-78743 and Japanese Patent No. 4189440, determination of the motivation of a user has not been studied by using the event-related potential starting from the point in time at which a problem is presented and the event-related potential starting from the point in time at which the solution to the problem is received. Therefore, there is a difficulty to improve the learning effect.

One non-limiting and exemplary embodiment provides a learning system, a learning method, a storage medium, and an apparatus capable of improving the learning effect.

In one general aspect, the techniques disclosed here feature a learning system including an output unit that outputs, to a user, a first problem and a display message prompting the user to take a break, an acquisition unit that acquires an answer to the first problem from the user, an electroencephalogram measurement unit that measures an electroencephalogram of the user, and a control unit. The control unit determines whether a first motivation of the user is present on the basis of a first event-related potential included in the electroencephalogram and starting from a point in time at which the first problem is output (a), determines whether a second motivation of the user is present on the basis of a second event-related potential included in the electroencephalogram and starting from a point in time at which the answer is acquired (b), and instructs the output unit to output a display message prompting the user to take a break if the first motivation is not present and the second motivation is not present (c).

It should be noted that general or specific embodiments may be implemented as a system, a method, an integrated circuit, a computer program, a computer-readable nonvolatile storage medium, such as a compact disc-read only memory (CD-ROM), or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Definitions

Definitions of the terms according to the embodiments of the present disclosure are provided first.

"Event-related potential (ERP)" is a fluctuation in the potential in an electroencephalogram (EEG) generated in response to a stimulus.

"Latency" is a time period from the time a stimulus (for example, an auditory stimulus or a visual stimulus) that generates an event-related potential is presented until the peak potential of a positive component or a negative component of an event-related potential appears.

"Negative component" generally refers to a potential lower than 0 µV. When there is a target for comparison of the potential, a potential having a more negative value is also referred to as a negative component.

"Positive component" generally refers to a potential greater than 0 µV. When there is a target for comparison of the potential, a potential having a more positive value is also referred to as a positive component.

As used herein, in order to define the component of the event-related potential, a point in time at which a predetermined period of time has elapsed since a certain point in time is expressed as a "latency of about 100 ms", for example. This means that the latency has a certain range centered on a specific time of 100 ms. According to Table 1 on Page 30 of "Event-related potential (ERP) Manual— mainly concerning P300—" (Edited by Kimitaka KAGA et al., Shinohara Shuppan Shinsha, 1995), in general, there is a difference (a deviation) of 30 ms to 50 ms among the waveforms of the event-related potentials for individuals. Accordingly, as used herein, the terms "about X ms" or "around X ms" indicate a time range having a duration of 30 ms to 50 ms before and after X ms (e.g., 100 ms±30 ms, or 200 ms±50 ms).

Underlying Knowledge Forming Basis of the Present Disclosure

An experiment conducted following the discovery of the underlying knowledge forming the basis of the present disclosure is described below. This experiment was conducted to detect the motivation of a user under a situation where the user was operating a device.

Figure 1:
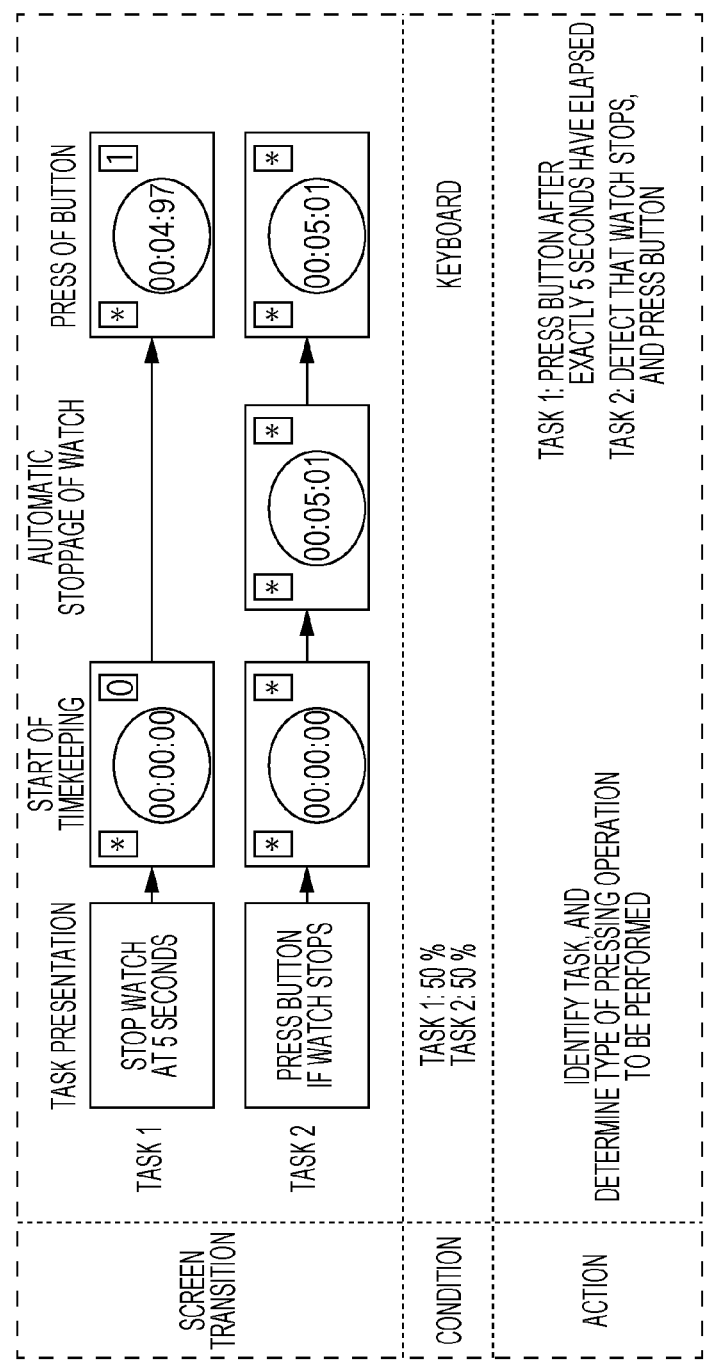
FIG. 1 is a schematic illustration of the procedure for an experiment conducted by the present inventors.

FIG. 1 is a schematic illustration of the procedure for the experiment.

In the experiment, the participants carried out two kinds of tasks. One of the two kinds of tasks was a task of stopping a watch (more specifically, a stopwatch) at exactly a predetermined time (5 seconds) (hereinafter referred to as "task 1"). The other kind of task was the following. That is, a watch (more specifically, a stopwatch) automatically stopped after a certain period of time (5 seconds) elapsed. Then, the participants confirmed the stoppage of the watch and pressed the button of the watch (hereinafter referred to as "task 2").

Task 1 consists of the following steps: presenting the task, starting timekeeping, and pressing the button. In presenting the task, the details of task 1 are presented to the participants. In starting timekeeping, a stopwatch used for task 1 is displayed, and the timekeeping using the stopwatch is started. In pressing the button, the participant stops the stopwatch at the scheduled time. Task 2 consists of the following steps: presenting the task, starting timekeeping, automatically stopping the watch, and pressing the button. In presenting the task, the details of task 2 are presented to the participants. In starting timekeeping, a stopwatch used for task 2 is displayed, and timekeeping using the stopwatch is started. In automatically stopping the watch, the stopwatch automatically stops after a certain period of time (5 seconds) has elapsed since the start of timekeeping. In pressing the button, the participant presses the button after the stopwatch has stopped.

In terms of task 1, as described in Kou Murayama, et. al, "Neural basis of the undermining effect of monetary reward on intrinsic motivation", PNAS 107 (49), 20911-20916, 2010 (hereinafter referred to as "Non-Patent Literature (NPL) 1"), it was found that a motivation-related part of the brain is activated as a result of the brain function measurement using fMRI (functional Magnetic Resonance Imaging). That is, it was found that task 1 is a task that can motivate the participant. In contrast, in terms of task 2, it was found that the motivation-related part of the brain is not activated. That is, as described in NPL 1, it was found that task 2 is a task that does not motivate the participant.

In the experiment, one of task 1 and task 2 is randomly selected with a probability of 50%, and the details of the selected task are presented. For example, if task 1 is selected, the details of the task, namely, "Stop the watch at 5 seconds" are presented. If task 2 is selected, the details of the task, namely, "Press the button when the watch stops" are presented. The participant identifies which of the tasks 1 and 2 has been presented and determines the action thereof at the time of pressing the button. Thereafter, the participant presses the button by using a keyboard so that the timing at which the button is pressed is the determined timing, that is, the timing according to the details of the presented task. More specifically, in task 1, the participant presses the button for the stopwatch to stop at exactly 5 seconds. In task 2, the participant presses the button after confirming that the stopwatch has automatically stopped.

There were seven participants in the experiment. In the experiment, task 1 (30 tests) and task 2 (30 tests) were performed for each of the seven participants.

The participants were apprised of the procedure for task 1 and the procedure for task 2 in advance. When task 1 was presented to the participant, the participant performed the operation according to the procedure for task 1. When task 2 was presented to the participant, the participant performed the operation according to the procedure for task 2. Task 1 and task 2 were randomly presented to participants.

Figure 2A:
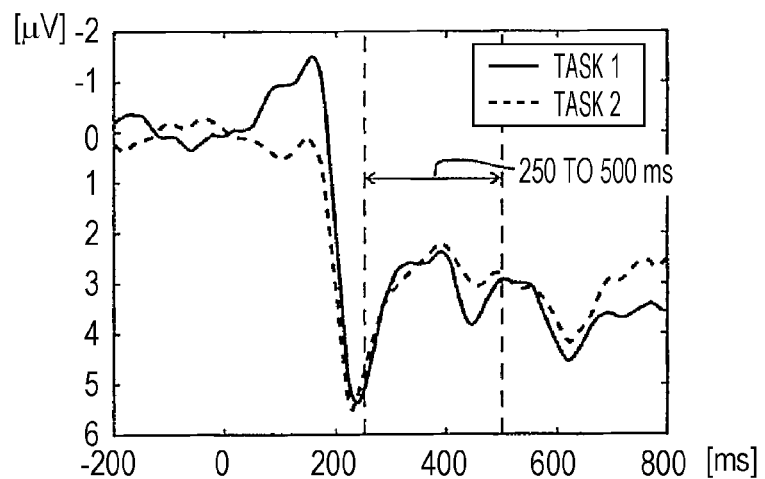
FIG. 2A illustrates a fluctuation of an event-related potential for each of kinds of tasks at the time of task presentation.
Figure 2B:
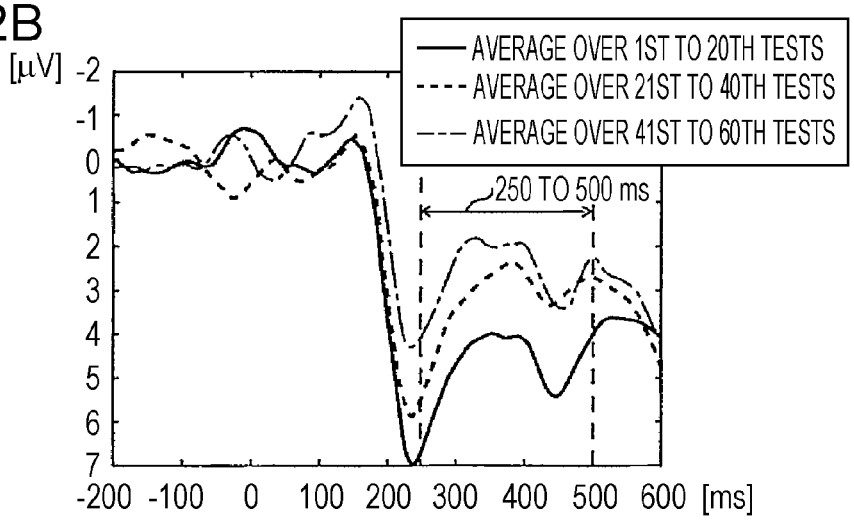
FIG. 2B illustrates fluctuations of an event-related potential for the numbers of the tests at the time of task presentation.
Figure 2C:
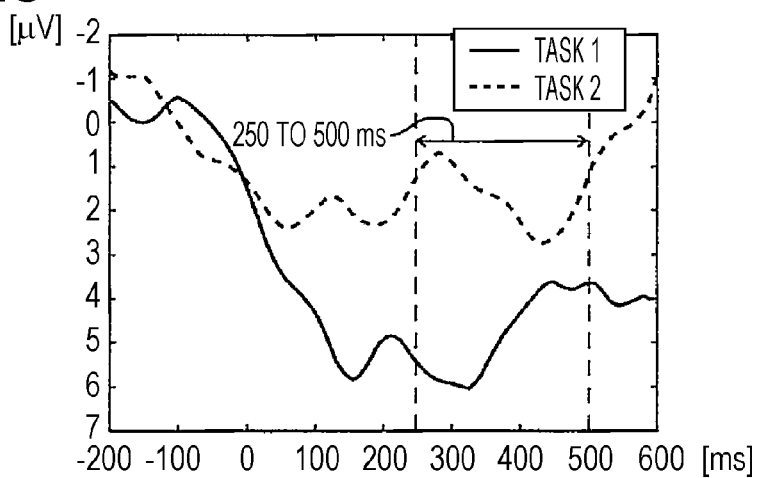
FIG. 2C illustrates a fluctuation of an event-related potential for each of kinds of tasks at the time of inputting an answer.

FIGS. 2A to 2C illustrate the result of the measurement of the electroencephalograms when task 1 and task 2 are performed. In FIGS. 2A to 2C, the abscissa represents the time (ms), and the ordinates represents the potential (µV). The sampling frequency was 1024 Hz.

FIG. 2A illustrates the electroencephalogram (the average over 30 tests) measured when task 1 was presented and the electroencephalogram (the average over 30 tests) measured when task 2 was presented. In FIG. 2A, the time when task 1 or task 1 is presented corresponds to 0 msec. As used herein, milliseconds are abbreviated as ms or msec.

Here, the electroencephalogram means the potentials for the entire duration regardless of whether task 1 or task 2 is presented. The event-related potential means the potential corresponding to the presentation of task 1 or task 2. The event-related potential here corresponds to the potential of 250 msec to 500 msec after task 1 or task 2 has been presented.

In FIG. 2A, the measured electroencephalogram include an event-related potential for task 1 (a solid line) and an event-related potential for task 2 (a broken line). The characteristic event-related potential (the electroencephalogram from 250 msec to 500 msec) here is in a range from 2.5 µV to 5 µV.

After the task (stimulation) has been presented, the positive potential (the event-related potential) induced at around 300 msec is called P300. P300 is thought to include the motivation for the task.

Because task 1 (30 tests) or task 2 (30 tests) is randomly presented, it is considered that the motivation of the participant when task 1 is presented and the motivation of the participant when task 2 is presented are at the same level. Therefore, in FIG. 2A, since the event-related potential for task 1 and the event-related potential for task 2 are at the same level, the experimental result in FIG. 2A indicates that the participant's motivation can be measured regardless of the kind of task.

FIG. 2B illustrates the electroencephalogram in each of the tests in which one of task 1 and task 2 was presented. In FIG. 2B, the time when task 1 or the issue 2 is presented corresponds to 0 msec. FIG. 2B is a graph illustrating the addition average value of the electroencephalograms of the 1st to 20th tests (a solid line), the average value of the electroencephalogram in the 21st to 40th tests (a broken line), and the average value of the electroencephalograms in the 41st to 60th tests (an alternate long and short dash line).

In FIG. 2B, the amplitude of the event-related potential measured when the number of tests of the task is large is smaller than the amplitude of the event-related potential measured when the number of tests is small. In general, participants are tired by continuing the tasks, so that the motivation decreases. That is, the motivation of the participant when the number of tests of the task is large is considered to be lower than the motivation of the participant when the number of tests is small.

Accordingly, it can be seen from the experimental results in FIG. 2B that the motivation of the participant before the task is presented can be measured.

As described above, from the results illustrated in FIGS. 2A and 2B, it can be seen that the event-related potential starting from the task presentation does not depend on the kind of task, and the motivation of the participant before the task is presented can be measured.

FIG. 2C illustrates the electroencephalogram for task 1 (the average of 30 tests) and the electroencephalogram for task 2 (the average of 30 tests). In FIG. 2C, the time when the answers to task 1 or the answers to task 2 are input corresponds to 0 msec. The time when each of the answers is input in task 1 or task 2 is defined as the time when the button is pressed.

After the answers to task 1 were input, the potential (the event-related potential) in the time window of 250 msec to 500 msec varied from 4 µV to 6 µV. After the answers to task 2 were input, the potential (the event-related potential) in the time window of 250 msec to 500 msec varied from 0.5 µV to 2.5 µV. Therefore, the amplitude of the event-related potential for task 1 is larger than the amplitude of the event-related potential for task 2.

As described above, it is found that the motivation for task 1 is higher than the motivation for task 2. That is, as can be seen from the event-related potential illustrated in FIG. 2C, the motivation at the time of inputting the answer to task 1 is higher than the motivation at the time of inputting the answer to task 2.

Accordingly, the present inventors found from the experimental results in FIG. 2C that the motivation for the kind or details of a task can be measured by using the event-related potential starting from the input of the answer to the task.

As described above, the present inventors found that different motivations can be measured by using the event-related potential starting from task presentation and the event-related potential starting from the input of the answer to the task.

According to the present disclosure, it is possible to speculate the cause of a decrease in the user's motivation by using the states of motivation determined from the event-related potentials at the above-described two different timings. Furthermore, by using the motivational states, the effect of learning can be improved.

That is, according to an aspect of the present disclosure, a learning system includes an output unit that outputs, to a user, a first problem and a display message prompting the user to take a break, an acquisition unit that acquires an answer to the first problem from the user, an electroencephalogram measurement unit that measures an electroencephalogram of the user, and a control unit. The control unit determines whether a first motivation of the user is present on the basis of a first event-related potential included in the electroencephalogram and starting from a point in time at which the first problem is output (a), determines whether a second motivation of the user is present on the basis of a second event-related potential included in the electroencephalogram and starting from a point in time at which the answer is acquired (b), and instructs the output unit to output a display message prompting the user to take a break if the first motivation is not present and the second motivation is not present (c).

Here, the point in time at which the first problem is output corresponds to the point in time at which a task is presented in the above-described experiment. Accordingly, the presence or absence of the motivation of the user before the first problem is output is determined as the presence or absence of the first motivation by using the first event-related potential starting from that point in time. In addition, the point in time at which the answer is acquired corresponds to the point in time at which the answer is input in the experiment. Therefore, from the second event-related potential starting at that point in time, the presence or absence of the user's motivation for the content of the first problem, which is the user's motivation after the answer is acquired, is determined as the presence or absence of the second motivation.

If the first motivation is not present and the second motivation is not present, it is highly likely that the user is in a state in which the user has no motivation before the first problem is presented and, in addition, the motivation is not improved even after the content of the first problem is presented, that is, the user is in a 'lack of motivation' state. It is difficult for such a user who is in a 'lack of motivation' state to obtain a sufficient learning effect even if the user repeats learning in which a problem is presented to the user and the user provides an answer to the problem. For this reason, in the learning system according to an aspect of the present disclosure, if the user is in a 'lack of motivation' state, a display message prompting the user to take a break is output. As a result, the motivation of the user can be recovered and, thus, the learning effect can be improved.

That is, the present inventors have developed a novel method for directly detecting the user's motivational state at the time of learning by using the event-related potential of the electroencephalogram. In order to solve the existing problem, according to the present disclosure, the user's motivation is determined from an event-related potential starting from each of two timings, that is, one timing at which a problem is output and the other timing at which an answer to the problem is acquired. Thereafter, the learning method is modified by using the determined motivation. As used herein, the term "modification of the learning method" refers to, for example, an operation of presenting a comment relating to the user's motivation to the user on the screen or changing a problem to be presented. By employing two types of determination results of the presence of motivation obtained at different timings through such a configuration, it can be determined whether the cause of a decrease in the motivation depends on the presented problem. If the motivation that has been decreased before the presentation of the problem is not recovered after the answer is acquired, a message for improving the motivation is presented on a screen. In this manner, the motivation can be improved. As a result, the learning effect can be improved.

In addition, according to the present disclosure, by using the user's motivation determined from the event-related potential of the electroencephalogram of the user, the cause of a decrease in the motivation of the user who solves the problem can be speculated. By changing the learning step while taking into account the cause of the decrease, the user's motivation can be improved. As a result, the learning effect can be improved.

For example, in (a), the first event-related potential starting from a point in time at which the first problem is presented may be extracted from the electroencephalogram (a1), and it may be determined whether the first motivation of the user is present on the basis of the first event-related potential (a2). In (b), the second event-related potential starting from a point in time at which the answer is acquired may be extracted from the electroencephalogram (b1), and it may be determined whether the second motivation of the user is present on the basis of the second event-related potential (b2).

In this manner, if the electroencephalogram are continuously measured by the electroencephalogram measurement unit and the measured electroencephalogram are recorded, the first event-related potential and the second event-related potential each in an appropriate time window can be accurately extracted. As a result, it can be appropriately determined whether each of the first motivation and the second motivation is present and, thus, the learning effect can be improved more.

In addition, in (a1), the control unit may extract the first event-related potential in a time window of 250 msec to 500 msec after the output of the first problem. Furthermore, in (b1), the control unit may extract the second event-related potential in a time window of 250 msec to 500 msec after the acquisition of the answer.

In this manner, it can be appropriately determined whether each of the first motivation and the second motivation is present.

Furthermore, the control unit may further determine whether the acquired answer is correct (d). In the case where the acquired answer is correct, the first motivation is present, and the second motivation is not present (e1), the control unit may instruct the output unit to output a second problem that is more difficult than the first problem to solve (f1).

In the case where a first motivation is present and a second motivation is not present, the user is in a state called a low motivational state. That is, it is highly likely that the motivation before the presentation of the first problem decreases due to the content of the first problem. The cause of the decrease in motivation is that the difficulty level of the first problem is too high or the difficulty level of the first problem is too low. However, if the user's answer is correct, the cause can be limited to the difficulty level of the first problem being too low. Therefore, in the learning system according to an aspect of the present disclosure, when the user is in a low motivational state and if the answer is correct, a second problem that is more difficult than the first problem to solve is output. In this manner, the motivation of the user can be recovered. As a result, the learning effect can be improved.

In addition, the control unit may further determine whether the acquired answer is correct (d). In the case where the acquired answer is incorrect, the first motivation is present, and the second motivation is not present (e2), the control unit may instruct the output unit to output a third problem that is easier than the first problem to solve (f2).

If the user is in a low motivational state and the user's answer is incorrect, the cause can be limited to the difficulty level of the first problem being too high. Therefore, in the learning system according to an aspect of the present disclosure, when the user is in a low motivational state and if the answer is incorrect, a third problem which is easier than the first problem to solve is output. In this manner, the motivation of the user can be recovered. As a result, the learning effect can be improved.

In addition, in (d), the control unit may refer to a database storing a plurality of problems each associated with a correct answer of the problem and determine whether the acquired answer is correct. In (f1), the control unit may refer to the database storing a plurality of problems each associated with a correct answer of the problem and instruct the output unit to output the second problem associated with a difficulty level that is higher than the difficulty level associated with the first problem.

In this manner, it can be appropriately determined whether the answer is correct and, in addition, the second problem which is more difficult than the first problem to solve can be appropriately output.

In addition, in (d), the control unit may refer to a database storing a plurality of problems each associated with a correct answer of the problem and determine whether the acquired answer is correct. In (f2), the control unit may refer to the database storing a plurality of problems each associated with a correct answer of the problem and instruct the output unit to output the third problem associated with a difficulty level that is lower than the difficulty level associated with the first problem.

In this manner, it can be appropriately determined whether the answer is correct and, in addition, the third problem which is easier than the first problem to solve can be properly output.

Furthermore, if the first motivation is present and the second motivation is not present (g), the control unit may further instruct the output unit to output a fourth problem having a difficulty level that differs from the difficulty level of the first problem (h). However, if the second motivation is present (i), the control unit may instruct the output unit to output a fifth problem having a difficulty level that is the same as the difficulty level of the first problem (j).

As described above, the cause of the user being in a low motivational state is that the difficulty level of the first problem is too high or too low. Therefore, in the learning system according to an aspect of the present disclosure, if the user is in a low motivational state, the fourth problem having a difficulty level that differs from the difficulty level of the first problem is output. In this manner, the probability of recovery of the user's motivation can be increased. As a result, the learning effect can be improved. Furthermore, if the second motivation is present, the user is in a state called a normal state. That is, it is highly likely that the motivation that is present before the presentation of the first problem is maintained without being decreased by the content of the first problem. Alternatively, it is highly likely that a motivation that is not present before the presentation of the first problem is recovered due to the content of the first problem. Accordingly, the difficulty level of the first problem is suitable for maintaining or recovering the user's motivation. Therefore, in the learning system according to an aspect of the present disclosure, if the user is in a normal state, the fifth problem having a difficulty level that is the same as the difficulty level of the first problem is output. In this manner, the motivation of the user in a normal mode can be maintained or recovered. As a result, the learning effect can be improved.

In addition, in (h), the control unit may refer to a database storing a plurality of problems each associated with a difficulty level of the problem and instruct the output unit to output the fourth problem associated with a difficulty level that is lower or higher than the difficulty level associated with the first problem. In (j), the control unit may refer to the database and instruct the output unit to output the fifth problem associated with a difficulty level that is the same as the difficulty level associated with the first problem.

In this manner, the fourth problem having a difficulty level that differs from the difficulty level of the first problem can be properly output. In addition, the fifth problem having a difficulty level that is the same as the difficulty level of the first problem can be appropriately output.

Such a learning system according to the present disclosure relates to a system for providing a service or information to a user of, for example, a terminal device. In particular, the learning system relates to a technique for determining the motivation of a user in repeatedly performing a specific task, such as solving a problem, and allowing a more appropriate service to be provided to the user on the basis of the determined motivation.

Exemplary embodiments are described in detail below with reference to the accompanying drawings.

It is to be noted that each of the embodiments described below is a general or specific example of the present disclosure. A value, a shape, a material, a constituent element, the positions and the connection form of the constituent elements, steps, and the sequence of steps in the embodiments described below are only examples and shall not be construed as limiting the scope of the present disclosure. In addition, among the constituent elements in the embodiments described below, the constituent element that does not appear in an independent claim, which has the broadest scope, is described as an optional constituent element.

In addition, all of the drawings are schematic and not necessarily to scale. Furthermore, the same reference numerals are used throughout the accompanying drawings to refer to the same or similar constituent members.

First Exemplary Embodiment

System Configuration

Figure 3:
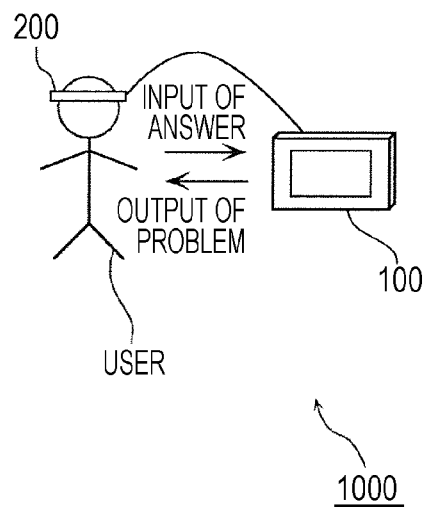
FIG. 3 illustrates an example of the external configuration of a learning system according to a first exemplary embodiment.

FIG. 3 illustrates an example of the external configuration of a learning system according to the first exemplary embodiment.

A learning system 1000 includes a terminal device 100 and an electroencephalograph 200. A user is attached to the electroencephalograph 200, and the user operates the terminal device 100. More specifically, the terminal device 100 outputs a problem. That is, the problem is presented to the user. By operating the terminal device 100, the user inputs an answer to the problem. Thus, the terminal device 100 acquires the answer. The problem output from the terminal device 100 corresponds to the task in the above-described experiment. By using the electroencephalograph 200, the terminal device 100 determines the presence of the motivations of the user on the basis of a first event-related potential starting from the point in time at which the problem is presented and a second event-related potential starting from the point in time at which the answer is acquired and performs processing in accordance with the result of determination. Note that the terminal device 100 may be a tablet terminal, a smartphone, a personal computer, for example.

Figure 4:
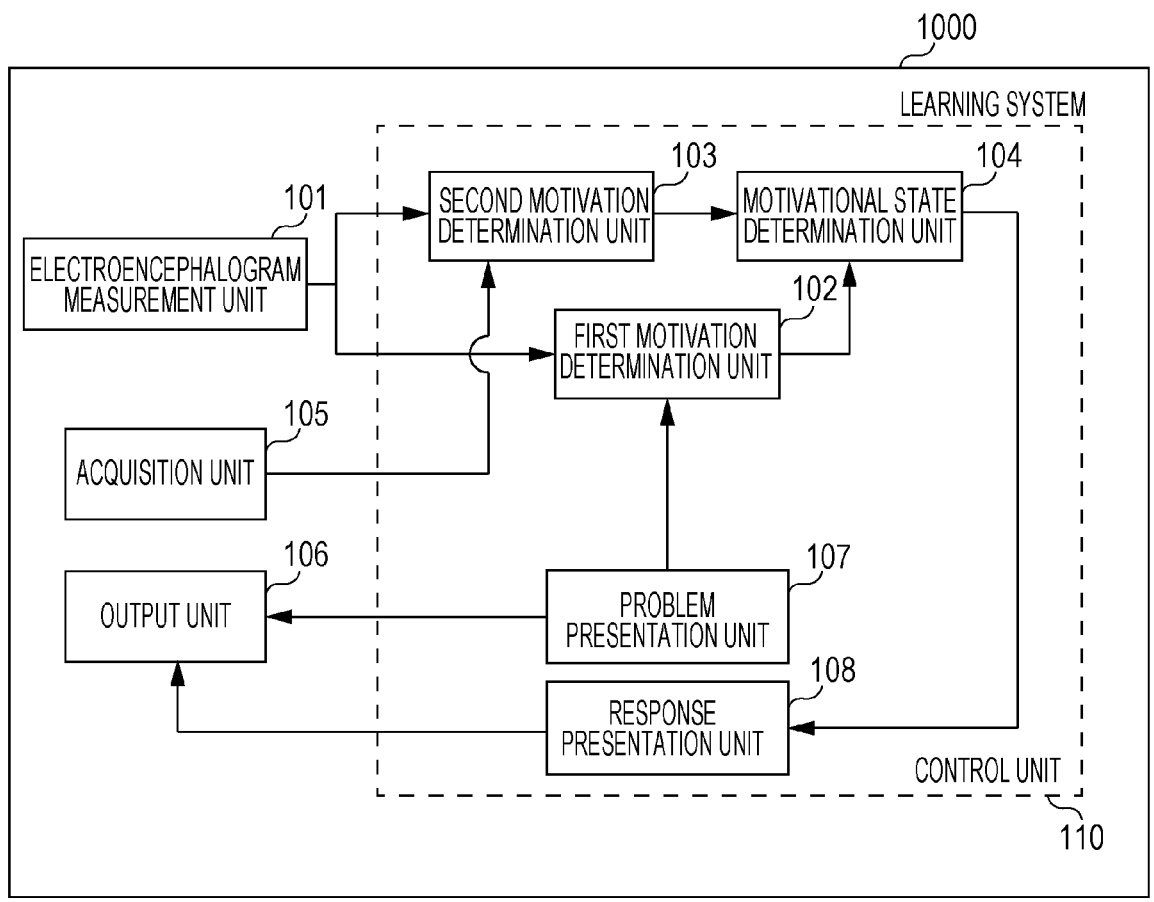
FIG. 4 illustrates an example of the functional configuration of the learning system according to the first exemplary embodiment.

FIG. 4 illustrates an example of the functional configuration of the learning system 1000 according to the first exemplary embodiment.

The learning system 1000 illustrated in FIG. 4 includes an electroencephalogram measurement unit 101, a first motivation determination unit 102, a second motivation determination unit 103, a motivational state determination unit 104, an acquisition unit 105, an output unit 106, a problem presentation unit 107, and a response presentation unit 108. Note that the first motivation determination unit 102, the second motivation determination unit 103, the motivational state determination unit 104, the problem presentation unit 107, and the response presentation unit 108 are constituent elements included in a control unit 110. The control unit 110 is configured as at least one processor, for example. In addition, the constituent elements other than the electroencephalogram measurement unit 101 included in the learning system 1000 are provided in the terminal device 100. For example, the electroencephalogram measurement unit 101 is formed from an electroencephalograph 200 and part of the function of the terminal device 100. Note that the part of the function may be included in the control unit 110 of the terminal device 100. In addition, all of the functions of the electroencephalogram measurement unit 101 may be included in the control unit 110 of the terminal device 100.

Output Unit

The output unit 106 outputs, to the user, a problem and a display message prompting the user to take a break. The problem is a problem selected by the problem presentation unit 107. In addition, the output unit 106 outputs a response selected by the response presentation unit 108. More specifically, the output unit 106 is, for example, a liquid crystal display or an organic electroluminescence (EL) display. The output unit 106 displays an image having information corresponding to a signal from the problem presentation unit 107 or the response presentation unit 108. That is, the output unit 106 outputs the problem selected by the problem presentation unit 107 as an image. Alternatively, the output unit 106 outputs the response selected by the response presentation unit 108 as an image. Note that the output unit 106 may be a loudspeaker and may output sounds according to a signal from the problem presentation unit 107 or the response presentation unit 108.

Acquisition Unit

The acquisition unit 105 acquires the user's answer to the problem. More specifically, the acquisition unit 105 is realized by part of the function of the processor and the hardware. The hardware is, for example, a unit for receiving the operation performed by the user, such as a keyboard, a mouse, a remote controller, or a microphone, that is, a unit for the user to input a request to the learning system 1000. It should be noted that the acquisition unit 105 may be realized by part of the function of the processor. The acquisition unit 105 notifies the second motivation determination unit 103 of the timing at which the answer is acquired.

Electroencephalogram Measurement Unit

The electroencephalogram measurement unit 101 measures the electroencephalogram of the user. The electroencephalogram measurement unit 101 is realized by the electroencephalograph 200 and part of the function of the processor. Alternatively, the electroencephalogram measurement unit 101 may be realized by a part of the function of the processor. In such a case, the electroencephalogram measurement unit 101 measures the electroencephalogram of the user by receiving a signal output from the electroencephalograph 200. Note that as described above, the electroencephalograph 200 is attached to the user in advance such that the electroencephalogram of the user can be acquired. The electroencephalograph 200 may include a first electrode to be attached to the user's scalp or forehead and a ground electrode to be attached to the user's ear. The electroencephalogram of the user measured and output by the electroencephalogram may indicate the time series change in the "voltage value between the ground electrode and the first electrode" with reference to the ground electrode. That is, there is a one-to-one correspondence between the plurality of voltage values indicated by the electroencephalogram and the plurality of points in time at which the plurality of voltage values are measured.

Problem Presentation Unit

The problem presentation unit 107 selects a problem to be presented to the user and displays the problem on the output unit 106. For example, the problem presentation unit 107 refers to a database storing a plurality of problems and selects one of the problems to be presented to the user. In addition, the problem presentation unit 107 notifies the first motivation determination unit 102 of the timing at which the problem is displayed on the output unit 106, that is, the timing at which the problem is output. The problem presentation unit 107 may include the database. Alternatively, the control unit 110 may include the database. The database may be included in a memory.

First Motivation Determination Unit

The first motivation determination unit 102 determines whether the first motivation of the user is present on the basis of the first event-related potential that is included in the electroencephalogram and that starts at the point in time at which the problem is output. The electroencephalogram is the electroencephalogram of the user measured by the electroencephalogram measurement unit 101. In addition, the point in time at which the problem is output is the point in time at which the first motivation determination unit 102 receives the notification from the problem presentation unit 107.

More specifically, the first motivation determination unit 102 extracts, from the electroencephalogram, the first event-related potential starting from the point in time at which the problem is output. Thereafter, the first motivation determination unit 102 determines whether the first motivation of the user is present on the basis of the first event-related potential. More specifically, the first motivation determination unit 102 extracts the first event-related potential in a time window of 250 msec to 500 msec after the problem is output. More specifically, the first motivation is the motivation of the user before the problem is output, that is, before the problem is presented.

That is, by using the electroencephalogram of the user measured by the electroencephalogram measurement unit 101 from immediately after the problem presentation unit 107 presented the problem to the user, the first motivation determination unit 102 determines whether a motivation is present before the presentation of the problem (i.e., whether the first motivation is present).

Second Motivation Determination Unit

The second motivation determination unit 103 determines whether the second motivation of the user is present on the basis of the second event-related potential that is included in the electroencephalogram and that starts at the point in time at which the answer is acquired. The electroencephalogram is the electroencephalogram of the user measured by the electroencephalogram measurement unit 101. In addition, the point in time at which the answer is acquired is the point in time at which the second motivation determination unit 103 receives the notification from the acquisition unit 105.

More specifically, the second motivation determination unit 103 extracts, from the electroencephalogram, the second event-related potential starting from the point in time at which the answer is acquired. Thereafter, the second motivation determination unit 103 determines whether the second motivation of the user is present on the basis of the second event-related potential. More specifically, the second motivation determination unit 103 extracts the second event-related potential in a time window of 250 msec to 500 msec after the answer is acquired. More specifically, the second motivation is the motivation of the user after the answer is acquired, that is, after the answer is acquired or the answer is input.

That is, by using the electroencephalogram of the user measured by the electroencephalogram measurement unit 101 from immediately after the user inputs, to the acquisition unit 105, the answer to the problem, the second motivation determination unit 103 determines whether a motivation is present after the answer is input (i.e., whether the second motivation is present).

Method for Determining Presence of Motivation

As described above, the first motivation determination unit 102 determines whether the first motivation is present in a predetermined time window after the problem is presented by using the electroencephalogram of the user measured by the electroencephalogram measurement unit 101. For example, the predetermined time window is a range of about 250 ms to about 500 ms after the timing at which the output unit 106 outputs a problem. Similarly, the second motivation determination unit 103 determines whether the second motivation is present in a predetermined time window after the answer is input by using the electroencephalogram of the user measured by the electroencephalogram measurement unit 101.

The first motivation determination unit 102 and the second motivation determination unit 103 determine whether a motivation component is present by using, for example, the peak potential, the interval average potential, or the similarity to a template of the electroencephalogram waveform. The first motivation determination unit 102 and the second motivation determination unit 103 determine that a motivation component is present if the user's electroencephalogram has an event-related potential higher than or equal to a predetermined threshold value. As used herein, the term "motivation component" refers to an event-related potential higher than or equal to the predetermined threshold value.

For example, it may be determined whether the motivation component is present by comparing the interval average potential having a latency of about 400 msec with a predetermined threshold value. The interval average potential may be defined as an average potential in a time window of a latency of about 400 msec.

An example of the predetermined threshold value is 0 μV. An example of a time window of a latency of about 400 msec is a time window of 250 msec to 500 msec after stimulation is presented.

In addition, the first motivation determination unit 102 and the second motivation determination unit 103 may hold a template of an electroencephalogram waveform having a motivation component or a template of an electroencephalogram waveform having no motivation component. The first motivation determination unit 102 and the second motivation determination unit 103 may determine whether a motivation component is present on the basis of the similarity between the waveform of the measured electroencephalogram and the template.

As described above, as used herein, the "event-related potential higher than or equal to a predetermined threshold value" includes an event-related potential having a peak potential of a positive component in a time window of about 400-ms latency or an interval average potential higher than or equal to a predetermined criterion, an event-related potential having the amplitude of the positive component in a time window of about 400-ms latency that is larger than a predetermined criterion, and an event-related potential having a similarity to a template including a motivation component higher than or equal to a predetermined criterion.

In the case where the presence of motivation is determined by using a template, the identification rate is improved by creating and using a template for each of the users, so that the presence of motivation can be accurately determined. Accordingly, the operation accuracy of the response presentation unit 108 (described in more detail below) is improved and, thus, the usability of the learning system 1000 is more improved. Alternatively, the first motivation determination unit 102 may determine whether a positive component appears in the event-related potential in a time window of about 250 ms to 500 ms after the starting point defined as a timing at which a problem is presented by the problem presentation unit 107. If a positive component appears, the first motivation determination unit 102 may determine that the motivation is present. However, if a positive component does not appear, the first motivation determination unit 102 may determine that the motivation is not present. In addition, the second motivation determination unit 103 may determine whether a positive component appears in the event-related potential in a time window of about 250 ms to 500 ms after the starting point defined as a timing at which the answer is received by the acquisition unit 105 (i.e., the timing of inputting the answer). If a positive component appears, the second motivation determination unit 103 may determine that motivation is present. However, if a positive component does not appear, the second motivation determination unit 103 may determine that motivation is not present.

Motivational State Determination Unit

The motivational state determination unit 104 determines the motivational state of the user on the basis of the results of determination made by the first motivation determination unit 102 and the second motivation determination unit 103. More specifically, if a first motivation is not present and a second motivation is not present, the motivational state determination unit 104 determines that the motivational state of the user is not a normal state ("state 1" described below) but a 'lack of motivation' state ("state 2" described below). Note that the motivational state is a state defined by the presence or absence of the first motivation and the presence or absence of the second motivation.

Response Presentation Unit

The response presentation unit 108 selects a response related to the user's motivational state on the basis of the result of determination made by the motivational state determination unit 104 and outputs the selected response. More specifically, if the motivational state determination unit 104 determines that the motivational state of the user is a 'lack of motivation' state, the response presentation unit 108 causes the output unit 106 to output the above-described display message prompting the user to take a break. That is, the response presentation unit 108 selects, as a response related to the user's motivational state, a display message prompting the user to take a break.

Hardware Configuration

Figure 5:
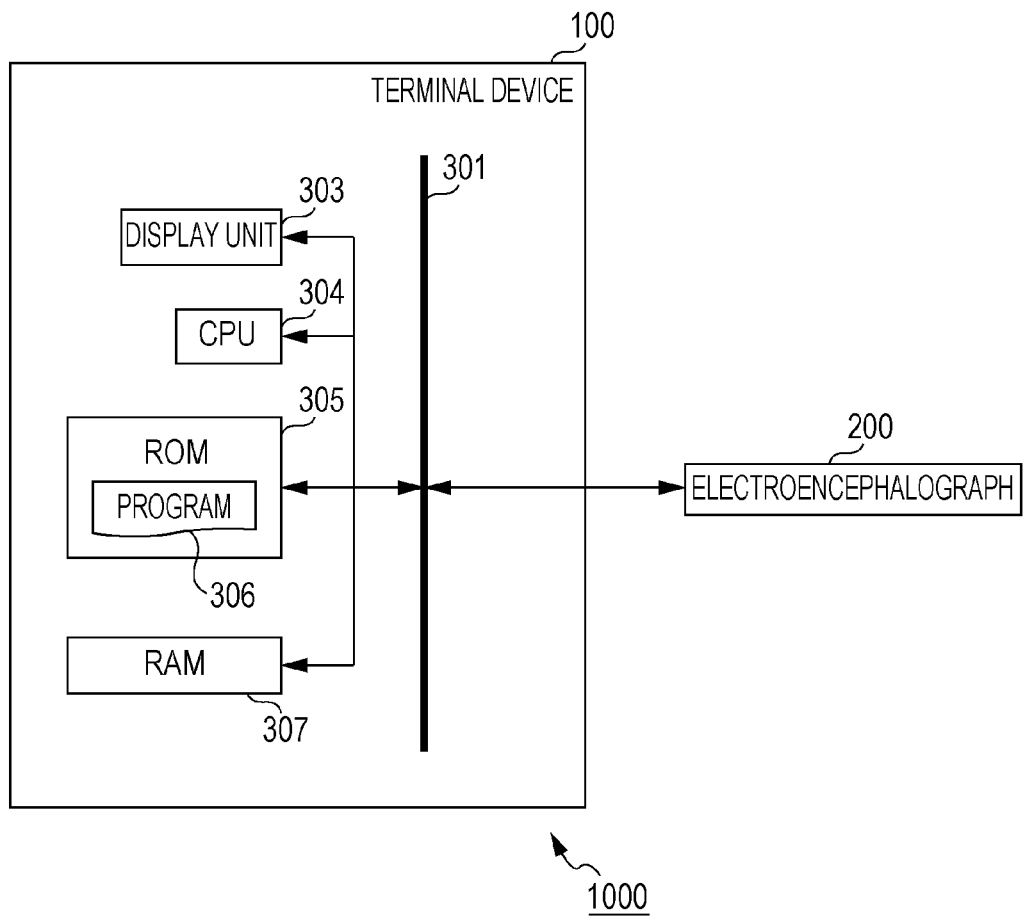
FIG. 5 illustrates an example of the hardware configuration of the learning system according to the first exemplary embodiment.

FIG. 5 illustrates an example of the hardware configuration of the learning system 1000 according to the first exemplary embodiment.

The terminal device 100 includes a display unit 303, a central processing unit (CPU) 304, a read only memory (ROM) 305, and a random access memory (RAM) 307, which are connected to one another via a bus 301. In addition, the electroencephalograph 200 is connected to the bus 301 of the terminal device 100. The display unit 303 is hardware corresponding to the above-described output unit 106. For example, the display unit 303 is formed from a liquid crystal display or an organic EL display. The CPU 304 is hardware corresponding to the control unit 110. In addition, the CPU 304 may execute the processing of each of the electroencephalogram measurement unit 101 and the acquisition unit 105. The ROM 305 stores, for example, a program 306 read and executed by the CPU 304. The CPU 304 executes the program 306 so as to perform the processing of the control unit 110. The RAM 307 temporarily stores data generated through the processing performed by the CPU 304. A database storing a plurality of problems may be placed in part of the ROM 305. A memory that allows a database storing a plurality of problems to be placed therein may be provided in the terminal device 100 and be connected to the bus 301.

The operation performed by the learning system 1000 having the above-described configuration according to the present exemplary embodiment is described below with reference to FIGS. 6 to 13.

Figure 6:
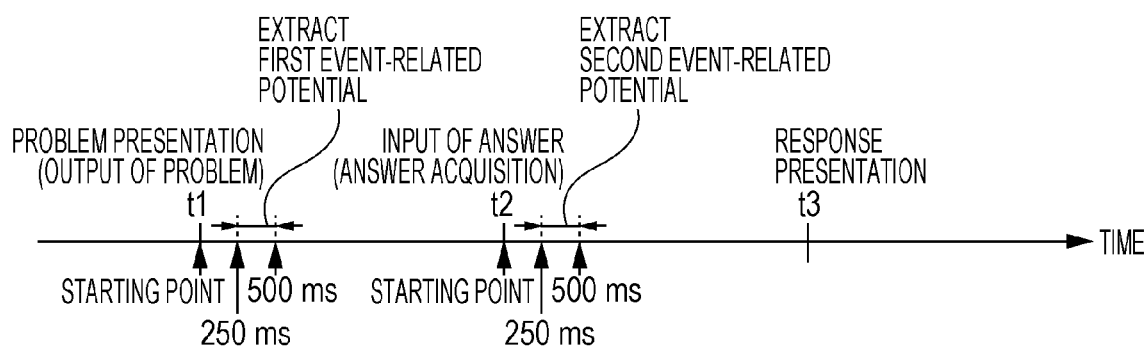
FIG. 6 illustrates the starting point and the time window of an event-related potential and the timing of response presentation according to the first exemplary embodiment.

Starting Point and Time window of Event-Related Potential and Timing of Response Presentation FIG. 6 illustrates the starting point and time window of the event-related potential and the timing of response presentation.

The first motivation determination unit 102 extracts, from the electroencephalogram measured by the electroencephalogram measurement unit 101, a first event-related potential starting from the point in time at which the problem is output, that is, a time t1 of the problem presentation. The first event-related potential starting from the time t1 is an event-related potential in the time window of the time when 250 ms has elapsed since the time t1 to the time when 500 ms has elapsed since the time t1.

The second motivation determination unit 103 extracts, from the electroencephalogram measured by the electroencephalogram measurement unit 101, the second event-related potential starting from the point in time at which a solution to the problem output at the time t1 is acquired, that is, a time t2 (>the time t1) of inputting the answer. The second event-related potential starting from the time t2 is an event-related potential in the time window of the time when 250 ms has elapsed since the time t2 to the time when 500 ms has elapsed from the time t2.

By using the output unit 106, the response presentation unit 108 presents, to the user, a response related to the user's motivational state determined on the basis of the extracted first event-related potential and second extracted event-related potential at a time t3 after the time t2. That is, response presentation based on the event-related potentials is performed at the time t3.

Figure 7:
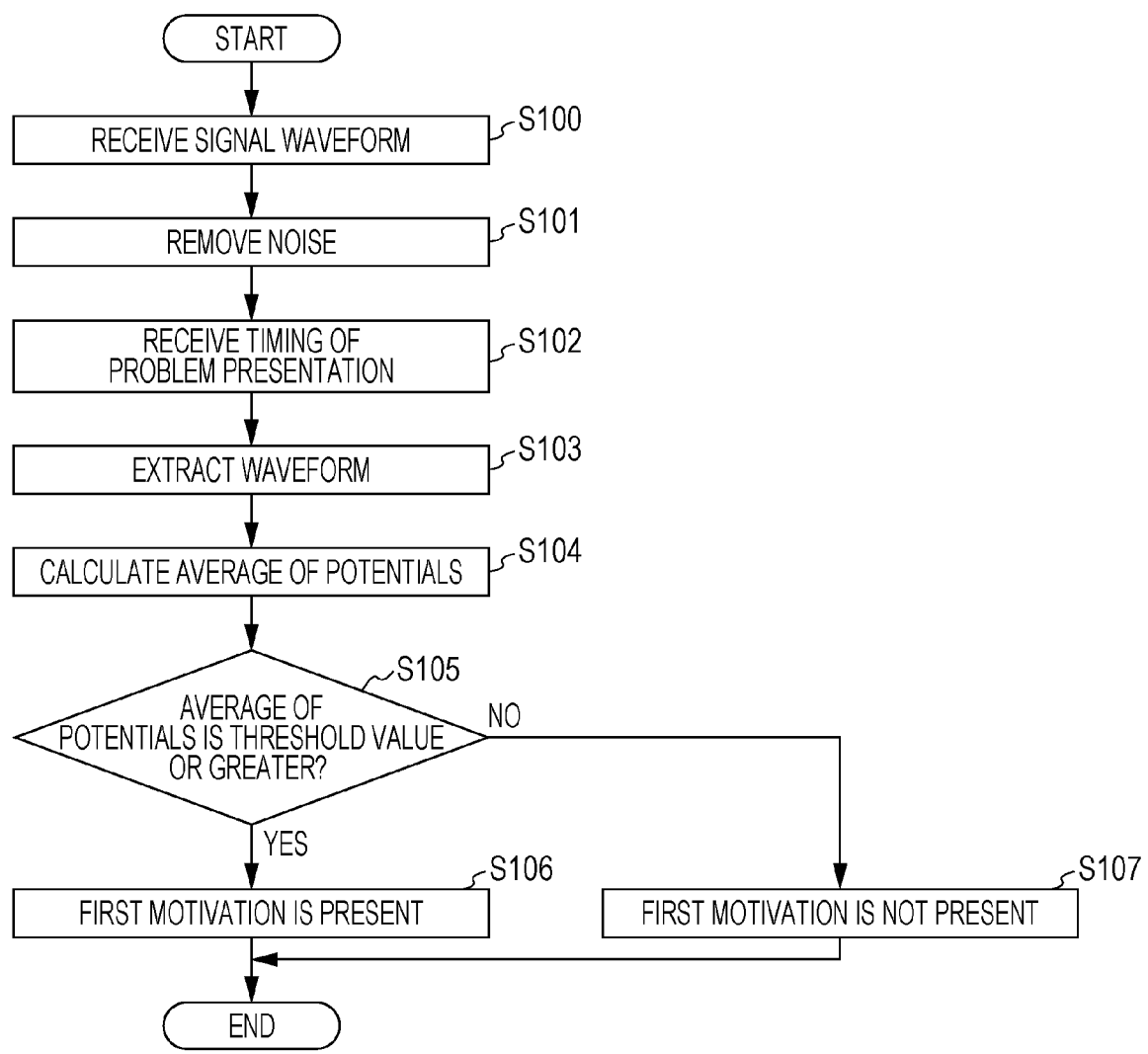
FIG. 7 is a flowchart illustrating an example of the processing performed by a first motivation determination unit according to the first exemplary embodiment.

Processing Performed by First Motivation Determination Unit and Second Motivation Determination Unit FIG. 7 is a flowchart illustrating an example of the processing performed by the first motivation determination unit 102.

(Step S100)

The first motivation determination unit 102 receives a signal waveform of the event-related potential from the electroencephalogram measurement unit 101. This signal waveform is the waveform of a brain wave. However, in some cases, the signal waveform may contain the waveform of noise. Note that the noise is generated from a variety of noise sources. Examples of the noise include device noise from the outside of the human body, myoelectricity noise and/or electro-oculogram noise from the inside of the human body, and background EEG that is not related to the problem presentation or answer input.

(Step S101)

The first motivation determination unit 102 performs noise removal processing to extract, from the received signal waveform, waveform information at a particular frequency. For example, the first motivation determination unit 102 performs a 30-Hz lowpass filtering process on the signal waveform and extracts an electroencephalogram corresponding to the waveform information at a particular frequency. In this manner, the noise is removed.

(Step S102)

Subsequently, the first motivation determination unit 102 receives, from the problem presentation unit 107, information indicating the timing at which the problem is presented to the user.

(Step S103)

The first motivation determination unit 102 extracts, from the signal waveform of the event-related potential subjected to noise removal in step S101, a waveform in a predetermined time window starting from the timing indicated by the information received in step S102. For example, the first motivation determination unit 102 may extract a waveform in a time window of 250 ms to 500 ms after the timing of problem presentation. The extracted waveform represents the first event-related potential.

(Step S104)

The first motivation determination unit 102 calculates an average value of the potentials of the waveform in the predetermined time window, which is extracted in step S103.

(Step S105)

The first motivation determination unit 102 determines whether the average potential calculated in step S104 is greater than or equal to a threshold value. The threshold value may be determined by using the template when a motivation is present. For example, each of the users may perform task 1 and task 2 illustrated in FIG. 1 in advance. Thereafter, the average value of the potentials in 10 tests for each of the tasks may be calculated, and the intermediate value of the average value for each of the tasks may be set as the threshold value. Alternatively, a value averaged from historical data of event-related potentials accumulated through the process of solving a problem may be set as the threshold value. In such a case, by creating and using a template for each of the users, the identification rate can be improved and, thus, it can be accurately determined whether motivation is present. Accordingly, the operation accuracy of the response presentation unit 108 is improved and, thus, the usability of the learning system 1000 is improved.

(Step S106)

If the result of determination in step S105 is YES (YES in step S105), the first motivation determination unit 102 determines that the first motivation is present.

(Step S107)

However, if the result of determination of step S105 is NO (NO in step S105), the first motivation determination unit 102 determines that the first motivation is not present.

Figure 8:
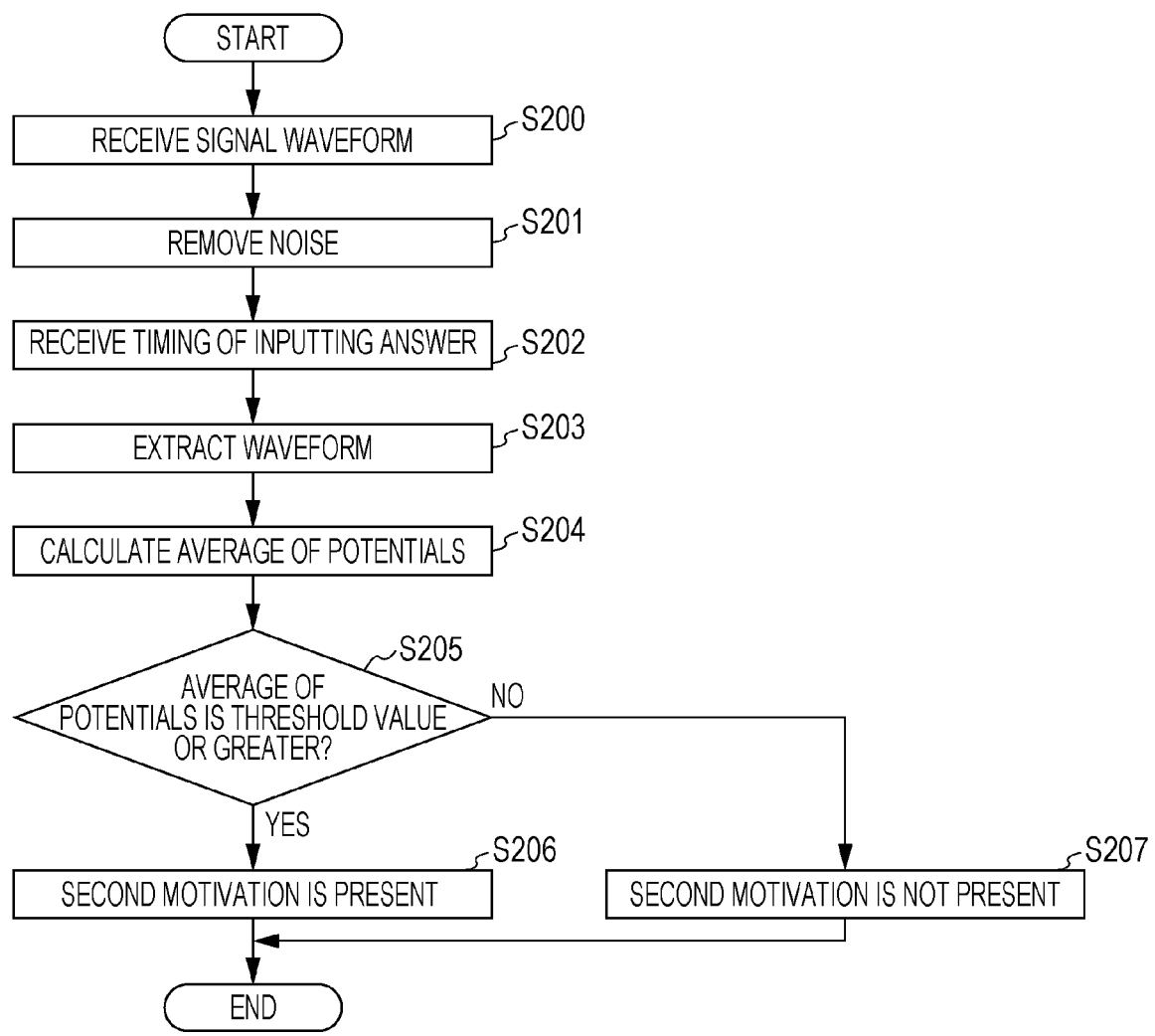
FIG. 8 is a flowchart illustrating an example of the processing performed by a second motivation determination unit according to the first exemplary embodiment.

FIG. 8 is a flowchart illustrating an example of the processing performed by the second motivation determination unit 103. Note that descriptions of steps identical to those in FIG. 7 are not repeated.

(Steps S200 to S201)

The second motivation determination unit 103 performs processing the same as in steps S100 to S101 illustrated in FIG. 7.

(Step S202)

The second motivation determination unit 103 receives, from the acquisition unit 105, information indicating the timing at which the user inputs the answer to the problem.

(Step S203)

The second motivation determination unit 103 extracts, from the signal waveform of the event-related potential subjected to noise removal in step S201, a waveform in a predetermined time window starting from the timing indicated by the information received in step S202. For example, the second motivation determination unit 103 may extract a waveform in the time window of 250 ms to 500 ms after the user inputs the answer to the problem. The extracted waveform represents the second event-related potential.

(Steps S204 to S205)

The second motivation determination unit 103 performs processing the same as in steps S104 to S105 illustrated in FIG. 7 on the waveform extracted in step S203.

(Step S206)

If the result of determination in step S205 is YES (YES in step S205), the second motivation determination unit 103 determines that the second motivation is present.

(Step S207)

However, if the result of determination in step S205 is NO (NO in step S205), the second motivation determination unit 103 determines that the second motivation is not present.

Motivational State

Figures 9, 10:
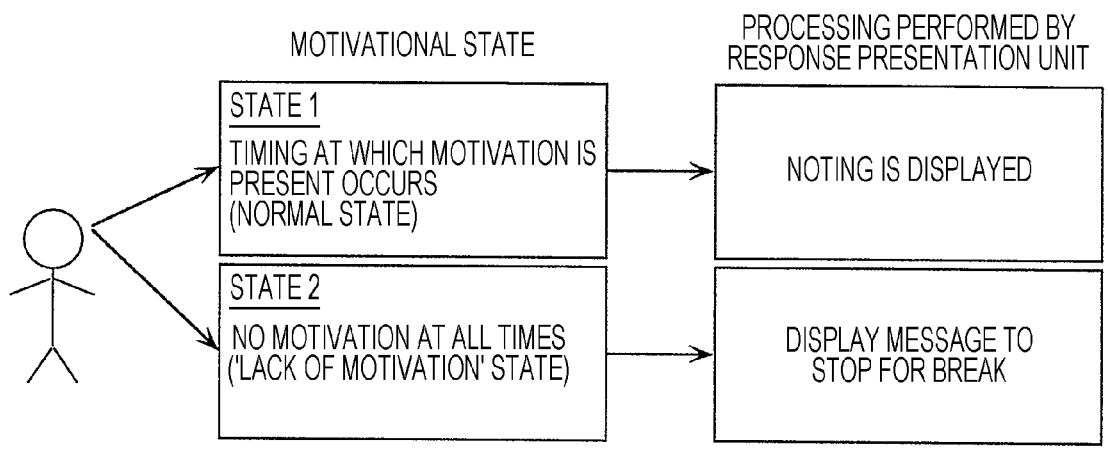
FIG. 9 illustrates the motivational states determined by a motivational state determination unit according to the first exemplary embodiment.
FIG. 10 illustrates the processing performed by a response presentation unit in accordance with each of the motivational states according to the first exemplary embodiment.

FIG. 9 illustrates the motivational state determined by the motivational state determination unit 104 according to the first exemplary embodiment. The motivational state determination unit 104 determines the motivational state of the user on the basis of the presence of the first motivation (the presence/absence of the motivation) determined by the first motivation determination unit 102 and the presence of the second motivation (the presence/absence of the motivation) determined by the second motivation determination unit 103.

More specifically, if the first motivation is "absent" and the second motivation is "absent", the motivational state determination unit 104 determines that the user's motivational state is a particular state (that is, state 2). In state 2, motivation is not present before presenting a certain problem, and motivation is not present even after inputting the answer to the problem. That is, in this state, motivation is not present before the user tackles the problem, and the user is not motivated to tackle the problem. According to the first exemplary embodiment, it is determined that state 2 is a particular state and that the other states are normal states (that is, state 1). That is, if at least one of the first motivation and the second motivation is "present", the motivational state determination unit 104 determines that the user's motivational state is a normal state (that is, state 1).

Presentation of Answer Corresponding to Motivational State

FIG. 10 illustrates the processing performed by the response presentation unit 108 in accordance with each of the motivational states according to the first exemplary embodiment. The response presentation unit 108 determines the information to be displayed by the output unit 106 in accordance with the result of determination made by the motivational state determination unit 104. More specifically, if the result of determination made by the motivational state determination unit 104 is state 2, the response presentation unit 108 determines, as the information to be displayed by the output unit 106, a message prompting the user to take a break. Thereafter, the response presentation unit 108 instructs the output unit 106 to display information (that is, a message) to prompt the user to take a break. The reason for displaying such a message is that if the user's motivational state is state 2, it is likely that the motivation of the user has been low for a long time. Thus, state 2 is also referred to as a 'lack of motivation' state. For example, as the message prompting the user to take a break, the response presentation unit 108 may use the particular message "You are tired. How about taking a break?", which prompts the user to take a particular action. Alternatively, as the message prompting the user to take a break, the response presentation unit 108 may use the message "You do not seem to be focusing on the problem", which notifies the user of their motivational state. In contrast, if the result of determination made by the motivational state determination unit 104 is state 1, the response presentation unit 108 instructs the output unit 106 to display nothing. The reason for displaying nothing is that if the user's motivational state is state 1, it is likely that the user is motivated at all times or the motivation of the user fluctuates in the process of tackling the presented problem. Thus, state 1 is also referred to as a normal state to distinguish state 1 from the 'lack of motivation' state.

Example of Display Screen

Figure 11:
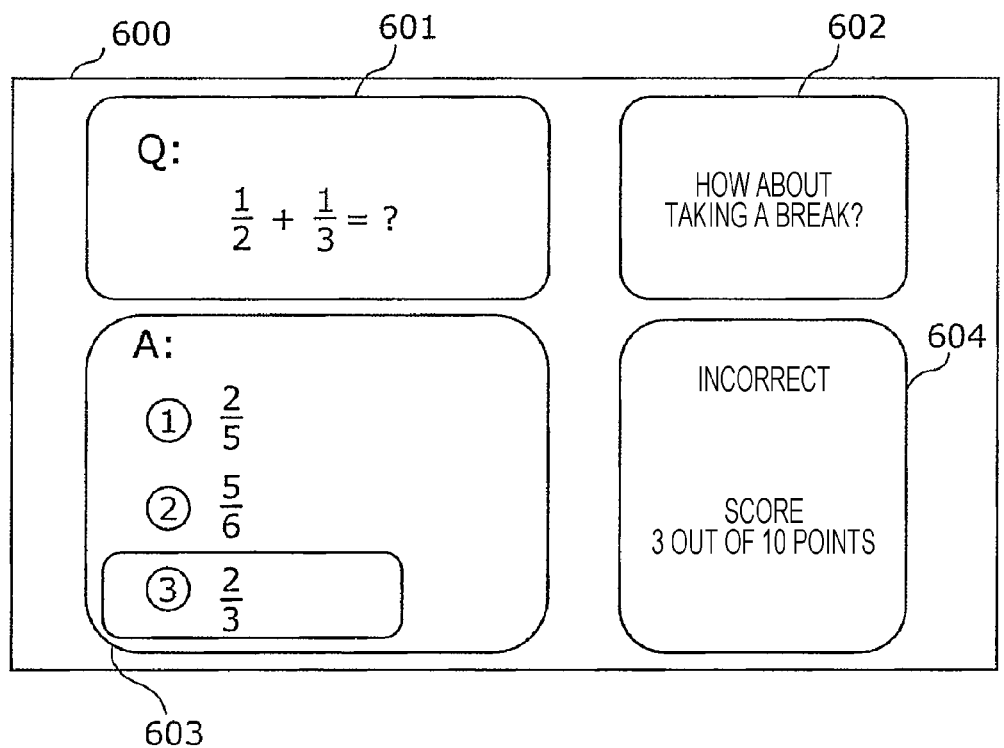
FIG. 11 illustrates an example of a screen displayed by an output unit according to the first exemplary embodiment.

FIG. 11 illustrates an example of a screen displayed by the output unit 106.

The output unit 106 displays a screen 600 including a problem presentation field 601, a response presentation field 602, an answer input field 603, and a true/false presentation field 604. In the problem presentation field 601, the problem selected by the problem presentation unit 107 is displayed. In the answer input field 603, the user's answer acquired by the acquisition unit 105 is displayed. In addition, in the answer input field 603, a plurality of options may be displayed. In such a case, any one of the plurality of options is selected as the user's answer acquired by the acquisition unit 105, and the selected one is displayed in the answer input field 603 in a manner that differs from the manner for the other options. In the true/false presentation field 604, information as to whether the user's answer to the displayed problem is correct or incorrect is displayed. In the response presentation field 602, the message determined by the response presentation unit 108 is displayed. For example, if the motivational state determination unit 104 determines that the user's motivational state is state 2, the message "How about taking a break?" is displayed in the response presentation field 602 as a message prompting the user to take a break.

As described above, according to the present exemplary embodiment, by combining the motivation before presenting a problem with the motivation after inputting the answer, a message prompting the user to take a break is displayed if the motivation that is not present before presenting the problem is not recovered after solving the problem. In this manner, the motivation can be improved and, thus, the learning effect can be improved.

Process Flow of Learning System

Figure 12:
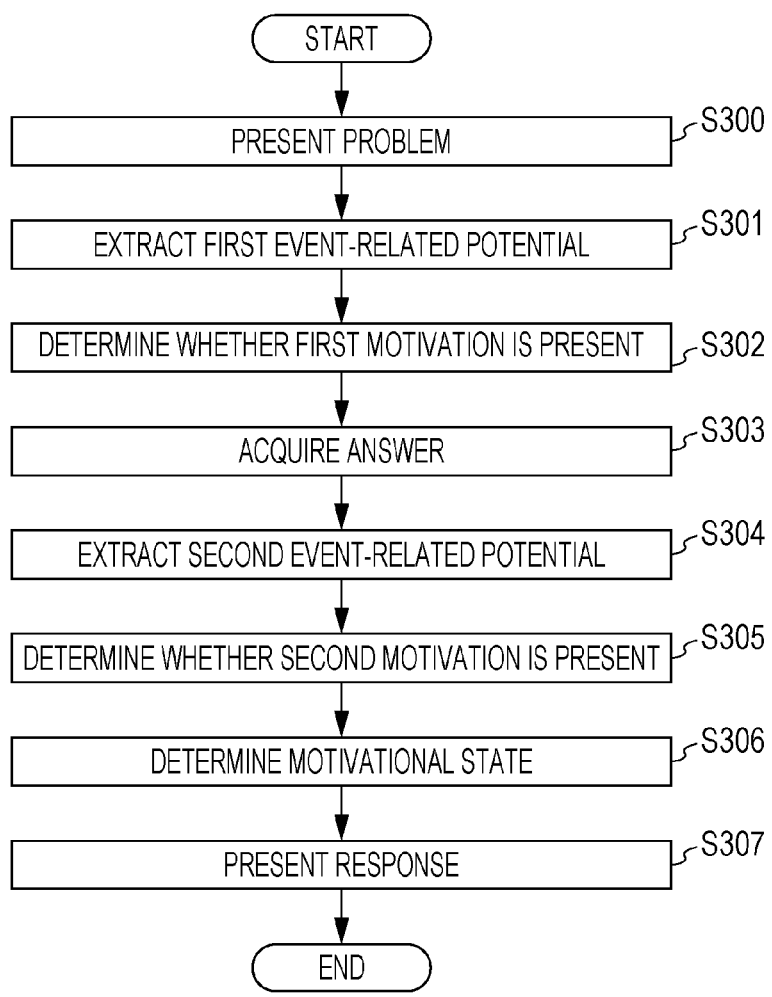
FIG. 12 is a flowchart illustrating an example of the processing performed by the learning system according to the first exemplary embodiment.

FIG. 12 is a flowchart illustrating an example of the processing performed by the learning system 1000 according to the present exemplary embodiment.

(Step S300)

The output unit 106 presents a problem selected by the problem presentation unit 107. At this time, the problem is displayed in the problem presentation field 601 of a screen 600 illustrated in FIG. 11.

(Step S301)

The first motivation determination unit 102 extracts, from the electroencephalogram measured by the electroencephalogram measurement unit 101, the first event-related potential in a predetermined time window starting from the time t1 at which a problem is presented illustrated in FIG. 6. In this case, for example, the electroencephalogram measurement unit 101 measures the user's electroencephalogram at all times and records the electroencephalogram in time series. The first motivation determination unit 102 extracts the first event-related potential from the recorded electroencephalogram. It should be noted that the electroencephalogram measurement unit 101 may measure the electroencephalogram in the above-described time window as the first event-related potential, and the first motivation determination unit 102 may acquire the first event-related potential from the electroencephalogram measurement unit 101 without extracting the first event-related potential.

(Step S302)

Subsequently, the first motivation determination unit 102 determines whether the motivation of the user (the above-described first motivation) for the problem presentation in step S300 is present on the basis of the first event-related potential extracted in step S301. This determination is made in accordance with the above-described "method for determining the presence/absence of motivation".

(Step S303)

Subsequently, the user inputs the answer to the problem displayed in the problem presentation field 601 of the screen 600 into the answer input field 603 of the screen 600. The input of the answer may be performed by selecting one of a plurality of options. By such input of the answer from the user, the acquisition unit 105 acquires the answer.

(Step S304)

The second motivation determination unit 103 extracts, from the electroencephalogram measured by the electroencephalogram measurement unit 101, the second event-related potential in the predetermined time window starting from the time t2 at which the answer is input illustrated in FIG. 6. As in step S301, even in such a case, the electroencephalogram measurement unit 101 measures the user's electroencephalogram at all times and records the electroencephalogram in time series. The second motivation determination unit 103 extracts the second event-related potential from the recorded electroencephalogram. It should be noted that the electroencephalogram measurement unit 101 may measure the electroencephalogram in the above-described time window as the second event-related potential, and the second motivation determination unit 103 may acquire the second event-related potential from the electroencephalogram measurement unit 101 without extracting the second event-related potential.

(Step S305)

Subsequently, the second motivation determination unit 103 determines whether the motivation of the user (the above-described second motivation) is present after the input of the answer in step S303 on the basis of the second event-related potential extracted in step S304. This determination is made in accordance with the above-described "method for determining the presence/absence of motivation".

(Step S306)

Subsequently, the motivational state determination unit 104 determines the motivational state of the user by using the result of determination as to whether the first motivation is present made by the first motivation determination unit 102 (step S302) and the result of determination as to whether the second motivation is present made by the second motivation determination unit 103 (step S305). That is, according to the present exemplary embodiment, the motivational state determination unit 104 determines which of state 1 and state 2 illustrated in FIG. 9 is the motivational state of the user.

(Step S307)

The response presentation unit 108 selects and outputs a response related to the user's motivational state on the basis of the result of determination made by the motivational state determination unit 104. According to the present exemplary embodiment, if it is determined that the motivational state is state 2, the response presentation unit 108 selects and outputs a message prompting the user to take a break. The output response is displayed in the response presentation field 602 of the screen 600 illustrated in FIG. 11 at the time t3 at which the response is presented illustrated in FIG. 6.

Figure 13:
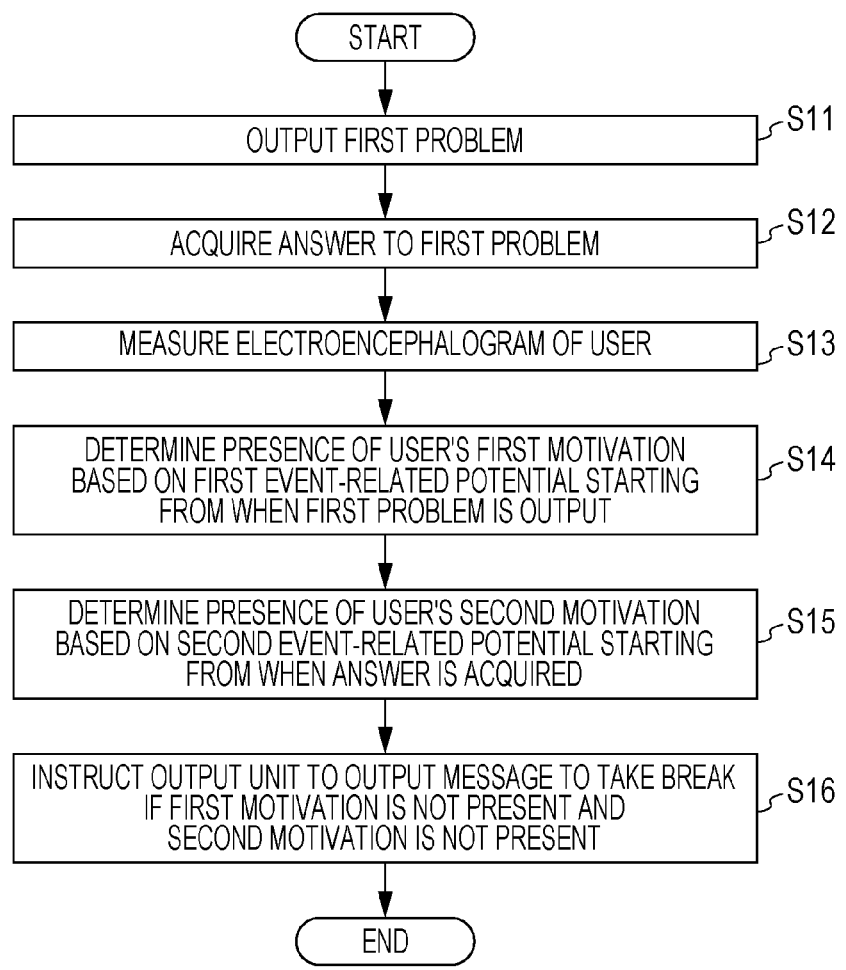
FIG. 13 is a flowchart illustrating a learning method according to an aspect of the present disclosure.

FIG. 13 is a flowchart of a learning method according to an aspect of the present disclosure.

In the flowchart illustrated in FIG. 12, each of the constituent elements included in the learning system 1000 executes one of the processes, but at least one processor may perform the learning method of the present disclosure.

The learning method according to the present disclosure is a learning method using a learning system having at least one processor and an output unit. In this learning method, processes in steps S11 to S16 are performed.

(Step S11)

The at least one processor outputs a first problem to the user via the output unit. The output unit is a device corresponding to the output unit 106. The output unit may be a display or a loudspeaker.

(Step S12)

The at least one processor acquires a user's answer to the first problem.

(Step S13)

The at least one processor measures the electroencephalogram of the user.

(Step S14)

The at least one processor determines whether the first motivation of the user is present on the basis of the first event-related potential included in the electroencephalogram and starting from the point in time at which the first problem is output.

(Step S15)

The at least one processor determines whether the second motivation of the user is present on the basis of the second event-related potential included in the electroencephalogram and starting from the point in time at which the answer is acquired.

(Step S16)

The at least one processor instructs the output unit to output a display message prompting the user to take a break if the first motivation is not present and the second motivation is not present.

Summary of First Exemplary Embodiment

The learning system 1000 according to the present exemplary embodiment includes the output unit 106 that outputs, to a user, a first problem and a display message prompting the user to take a break, the acquisition unit 105 that acquires an answer to the first problem from the user, the electroencephalogram measurement unit 101 that measures the electroencephalogram of the user, and the control unit 110. The control unit 110 determines whether a first motivation of the user is present on the basis of a first event-related potential included in the electroencephalogram and starting from a point in time at which the first problem is output (a). In addition, the control unit 110 determines whether a second motivation of the user is present on the basis of a second event-related potential included in the electroencephalogram and starting from a point in time at which the answer is acquired (b). Thereafter, the control unit 110 instructs the output unit 106 to output a display message prompting the user to take a break if the first motivation is not present and the second motivations is not present (c).

If the first motivation is not present and the second motivation is not present, it is highly likely that the user is in a state in which the user has no motivation before the first problem is presented and, in addition, the motivation is not improved even after the content of the first problem is presented, that is, the user is in a 'lack of motivation' state. It is difficult for such a user who has a 'lack of motivation' state to obtain a sufficient learning effect even if the user repeats learning in which a problem is presented to the user and the user provides an answer to the problem. For this reason, in the learning system 1000 according to the present exemplary embodiment, if the user has a 'lack of motivation' state, a display message prompting the user to take a break is output. As a result, the motivation of the user can be recovered and, thus, the learning effect can be improved.

In addition, in (a), the control unit 110 extracts, from the electroencephalogram, the first event-related potential starting from a point in time at which the first problem is presented (a1). Thereafter, the control unit 110 determines whether the first motivation of the user is present on the basis of the first event-related potential. In addition, in (b), the control unit 110 extracts, from the electroencephalogram, the second event-related potential starting from a point in time at which the answer is acquired (b1). Thereafter, the control unit 110 determines whether the second motivation of the user is present on the basis of the second event-related potential.

In this manner, if the electroencephalogram is continuously measured by the electroencephalogram measurement unit 101 and the measured electroencephalogram is recorded, the first event-related potential and the second event-related potential each in an appropriate time window can be accurately extracted. As a result, it can be appropriately determined whether each of the first motivation and the second motivation is present and, thus, the learning effect can be improved more.

In addition, in the above-mentioned (a1), the control unit 110 extracts the first event-related potential in a time window of 250 msec to 500 msec after the output of the first problem. Furthermore, in the above-mentioned (b1), the control unit 110 extracts the second event-related potential in a time window of 250 msec to 500 msec after the acquisition of the answer.

In this manner, it can be appropriately determined whether each of the first motivation and the second motivation is present.

Second Exemplary Embodiment

Unlike the first exemplary embodiment, according to the present exemplary embodiment, the operations of the response presentation unit 108 and the problem presentation unit are switched using the result of determination made by the motivational state determination unit. According to the first exemplary embodiment, when the motivation of the user is lowered because of the content of the presented problem, the motivation remains lowered. However, according to the present exemplary embodiment, the motivation can be improved by switching the difficulty level of the presented problem as described below. In this manner, in the case where the motivation is not present after inputting the answer, the motivation can be improved not only when motivation is not present before presenting the problem but also when motivation is present before presenting the problem. Thus, the motivation can be improved in the greater number of cases and, therefore, the learning effect can be improved.

System Configuration

Figures 14, 15:
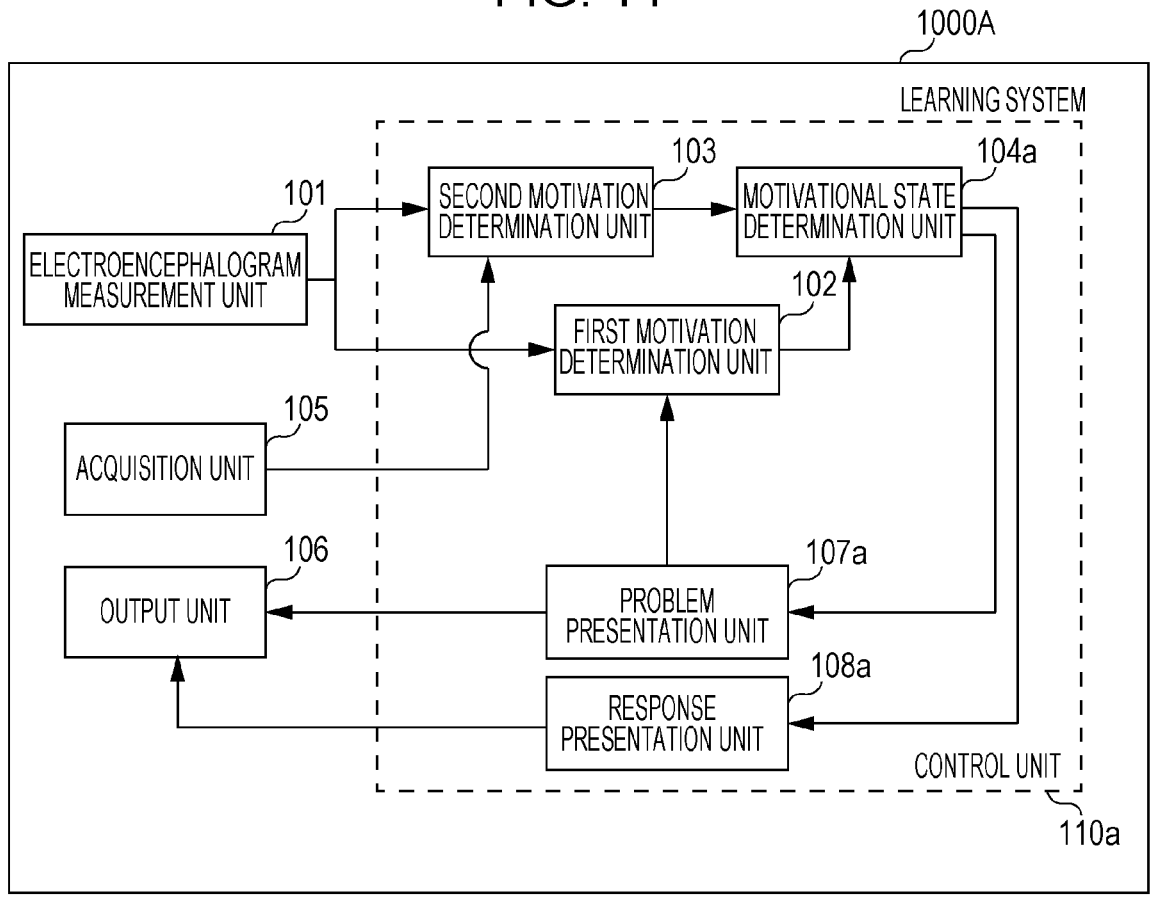
FIG. 14 illustrates an example of the functional configuration of a learning system according to a second exemplary embodiment.
FIG. 15 illustrates the motivational states determined by a motivational state determination unit according to the second exemplary embodiment.

FIG. 14 illustrates an example of the functional configuration of a learning system according to the second exemplary embodiment. According to the present exemplary embodiment, the same reference numerals are used to describe constituent elements that are the same as in the first exemplary embodiment, and detailed description of the constituent elements are not repeated.

A learning system 1000A according to the present exemplary embodiment includes a motivational state determination unit 104a, a problem presentation unit 107a, and a response presentation unit 108a instead of the motivational state determination unit 104, the problem presentation unit 107, and the response presentation unit 108 according to the first exemplary embodiment. Therefore, according to the present exemplary embodiment, the first motivation determination unit 102, the second motivation determination unit 103, the motivational state determination unit 104a, the problem presentation unit 107a, and the response presentation unit 108a are constituent elements included in a control unit 110a. Like the control unit 110 according to the first exemplary embodiment, the control unit 110a is configured as at least one processor, for example.

Motivational State Determination Unit

The motivational state determination unit 104a according to the present exemplary embodiment determines which of state 1, state 2, and a state 3 the user's motivational state is in accordance with the presence of each of the first motivation and the second motivation. Note that the motivational state determination unit 104 according to the first exemplary embodiment determines which of the normal state (state 1) and the 'lack of motivation' state (state 2) the user's motivational state is. That is, the motivational state determination unit 104a according to the present exemplary embodiment determines the user's motivational state in more detail than the motivational state determination unit 104 according to the first exemplary embodiment.

Motivational State

FIG. 15 illustrates the motivational state determined by the motivational state determination unit 104a according to the second exemplary embodiment. The motivational state determination unit 104a determines the motivational state of the user on the basis of the presence of the first motivation (the presence/absence of the motivation) determined by the first motivation determination unit 102 and the presence of the second motivation (the presence/absence of the motivation) determined by the second motivation determination unit 103.

More specifically, if the second motivation is "present", the motivational state determination unit 104a determines that the user's motivational state is state 1. If the first motivation is "absent" and the second motivation is "absent", the motivational state determination unit 104a determines that the motivational state of the user is state 3. However, if the first motivation is "present" and the second motivation is "absent", the motivational state determination unit 104a determines that the motivational state of the user is state 2. Here, state 1 is a normal state, state 2 is a low motivational state, and state 3 is a 'lack of motivation' state. Accordingly, the motivational state determination unit 104a according to the present exemplary embodiment determines whether the user's motivation state is in not only the normal state or the 'lack of motivation' state but also the low motivational state.

That is, according to the present exemplary embodiment, the determination as to whether the user's motivation state is the normal state or the 'lack of motivation' state is the same as in the first exemplary embodiment. However, the state in which the first motivation is "present" and the second motivation is "absent" (that is, the low motivational state) is distinguished from the normal state. In the low motivational state, although the user is motivated before presenting the problem, the motivation disappears in the period of time from the presentation of the problem to the input of the answer. That is, the low motivational state means that motivation has lowered in the process of producing an answer to the presented problem.

According to the present exemplary embodiment, the motivation of the user is improved by performing control so that an appropriate problem can be presented while switching the problem to be presented to the user who has a low motivational state.

Response Presentation Unit

The response presentation unit 108a according to the present exemplary embodiment selects and outputs a response related to the user's motivational state on the basis of the result of determination made by the motivational state determination unit 104a. More specifically, if the motivational state determination unit 104a determines that the motivational state of the user is a 'lack of motivation' state (that is, state 3), the response presentation unit 108a instructs the output unit 106 to output a display message prompting the user to take a break. At this time, as in the first exemplary embodiment, the response presentation unit 108a selects, as a response related to the user's motivational state, a display message prompting the user to take a break. However, if the motivational state determination unit 104a determines that the user's motivational state is the normal state or the low motivational state (that is, state 1 or state 2), the response presentation unit 108a instructs the output unit 106 to output nothing. That is, the output unit 106 does not display anything in the response presentation field 602 of the screen 600.

Problem Presentation Unit

The problem presentation unit 107a according to the present exemplary embodiment has the same function as the problem presentation unit 107 according to the first exemplary embodiment. However, if the motivational state determination unit 104a determines that the user is in a low motivational state (that is, state 2), the problem presentation unit 107a changes the difficulty level of a problem subsequently presented.

More specifically, if the first motivation is present and the second motivation is not present, the problem presentation unit 107a instructs the output unit 106 to output a problem (that is, a fourth problem) having a difficulty level that differs from the difficulty level of the current problem (that is, the first problem) as the next problem. If the second motivation is present, the problem presentation unit 107a instructs the output unit 106 to output a problem (that is, a fifth problem) having a difficulty level that is the same as the difficulty level of the current problem (that is, the first problem) as a next problem. More specifically, when instructing the output unit 106 to output the fourth problem, the problem presentation unit 107a refers to a database storing a plurality of problems each associated with one of the difficulty levels. Thereafter, the problem presentation unit 107a instructs the output unit 106 to output a fourth problem associated with a difficulty level lower or higher than the difficulty level associated with the first problem. In addition, when instructing the output unit 106 to output the fifth problem, the problem presentation unit 107a refers to the database. Thereafter, the problem presentation unit 107a instructs the output unit 106 to output the fifth problem associated with a difficulty level that is the same as the difficulty level associated with the first problem. Note that the database includes a plurality of problems and a plurality of pieces of difficulty level information, and there may be a one-to-one correspondence between the plurality of problems and the plurality of pieces of difficulty level information. When a problem i included in the plurality of problems ($1 \leq i \leq n$, where i and n are natural numbers) corresponds to a piece i of the difficulty level information, the piece i of the difficulty level information represents the difficulty level of the problem i. The piece i of the difficulty level information may be a natural number. When the piece i of the difficulty level information is a natural number, the difficulty level of the problem i corresponding to the piece i of the difficulty level information increases with decreasing number indicated by the piece i of the difficulty level information. That is, the problem is more difficult to solve with decreasing number. For example, the piece i of the difficulty level information may be determined by the creator of the problem i before the piece i of the difficulty level information is stored in the database. Other exemplary embodiments may employ the structure of a database that is the same as the structure described above. In addition, other exemplary embodiments may employ a method for determining difficulty level information that is the same as the method described above.

Note that the database may be provided in the learning system 1000A or the terminal device 100. Alternatively, the database may be provided in a server installed outside the learning system 1000A. The problem presentation unit 107a may include the database. The database may be included in the memory. When the database is provided in the server, the problem presentation unit 107a refers to the database in the server via, for example, the Internet.

Thus, unlike the learning system 1000 according to the first exemplary embodiment, the learning system 1000A according to the present exemplary embodiment controls the operations performed by the response presentation unit 108a and the problem presentation unit 107a on the basis of the motivational state determined by the motivational state determination unit 104a. That is, the motivational state determination unit 104a determines the motivational state of the user in accordance with the result of determination made by the first motivation determination unit 102 and the second motivation determination unit 103. Thereafter, the motivational state determination unit 104a sends the result of determination to the problem presentation unit 107a and the response presentation unit 108a. The problem presentation unit 107a and the response presentation unit 108a generate a problem and a response, respectively, in accordance with the user's motivational state sent from the motivational state determination unit 104a.

Figure 16:
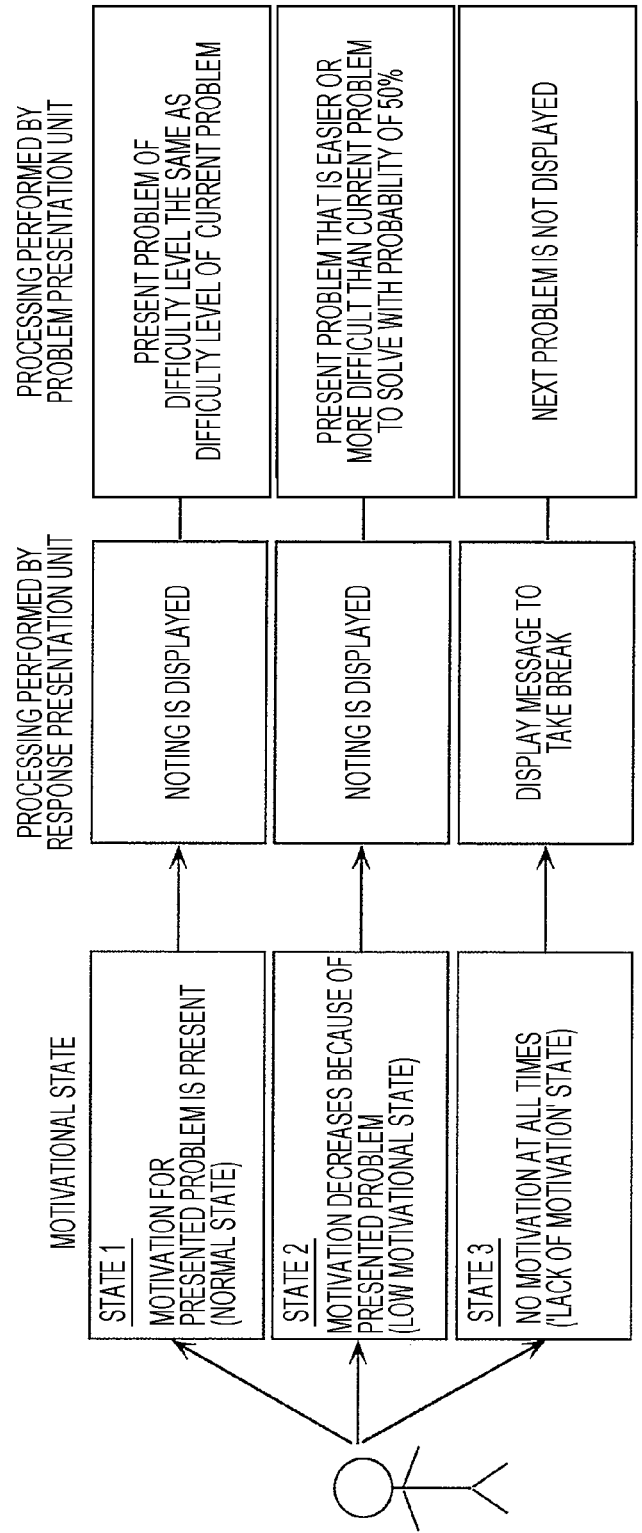
FIG. 16 illustrates the processing that corresponds to each of the motivational states and that is performed by a problem presentation unit and a response presentation unit according to the second exemplary embodiment.

Response Presentation and Problem Presentation Corresponding to Motivational State FIG. 16 illustrates the processing that corresponds to each of the motivational states and that is performed by the problem presentation unit 107a and the response presentation unit 108a according to the second exemplary embodiment.

The problem presentation unit 107a and the response presentation unit 108a determine the information to be displayed on the output unit 106 in accordance with the result of determination made by the motivational state determination unit 104a.

More specifically, the response presentation unit 108a displays nothing on the output unit 106 if the result of determination made by the motivational state determination unit 104a is state 1 or 2. The reason why nothing is displayed is that if the user's motivational state is state 1 or 2, it is likely that the user is motivated by the presented information about the problem or the motivation of the user is temporarily decreased in the process of answering the presented problem. Such state 1 is also referred to as a normal state, and state 2 is also referred to as a low motivational state.

However, if the result of determination made by the motivational state determination unit 104a is state 3, the response presentation unit 108a instructs the output unit 106 to output a display screen (that is, a message) prompting the user to take a break, as in the first exemplary embodiment. The reason for displaying such a message is that it is highly likely that the user's motivation remains low for a long time if the user's motivational state is state 3. Such state 3 is also referred to as a 'lack of motivation' state.

When the result of determination made by the motivational state determination unit 104a is state 1, the problem presentation unit 107a selects, as the next problem, a problem associated with a difficulty level that is the same as the difficulty level of the current problem. The reason for selecting a problem associated with the same difficulty level is that if the user's motivational state is state 1, it is highly likely that the user is motivated to tackle the problem.

If the result of determination made by the motivational state determination unit 104a is state 2, the problem presentation unit 107a selects, as the next problem, a problem having an attribute that differs from the attribute of the current problem. In this case, the attribute is the difficulty level of the problem. It should be noted that the attribute may be the subject or the course unit of the problem. For example, the problem presentation unit 107a selects one of a problem associated with a difficulty level easier (lower) than the difficulty level associated with the current problem and a problem associated with a difficulty level higher than the difficulty level associated with the current problem with a probability of 50%. The reason for selecting a problem associated with a difficulty level that differs from the difficulty level of the current problem is that if the user's motivational state is state 2, it is highly likely that although the user is motivated before the problem is presented, the motivation decreases because the content of the presented problem is not appropriate.

If the result of determination made by the motivational state determination unit 104a is state 3, the problem presentation unit 107a does not present the next problem. The reason for not presenting any problem is that if the user's motivational state is state 3, it is highly likely that the user is not motivated throughout the process of tackling the problem.

As described above, according to the present exemplary embodiment, when it is detected that the user is not motivated at the time of inputting the answer, it can be determined whether the motivation has decreased before the problem is presented or the motivation decreases because of the content of the problem using the presence/absence of motivation at the time of presenting the problem. That is, the user's motivational state can be determined depending on whether the state is state 2 or 3. In addition, according to the present exemplary embodiment, if motivation has decreased since the problem presentation, the user is prompted to take a break. However, if the motivation has decreased due to the content of the presented problem, the difficulty level of the subsequently presented problem is changed. Through such a control technique, the motivation of the user can be improved and, thus, the learning effect can be improved.

Process Flow of Learning System

Figure 17:
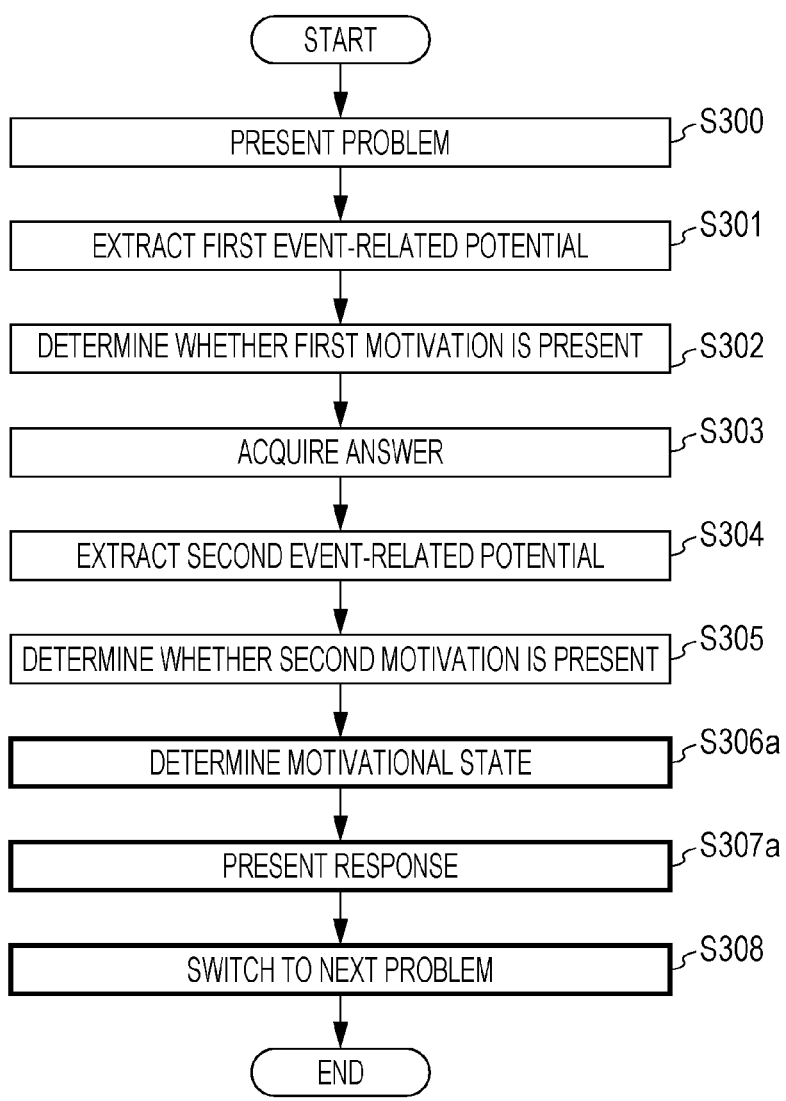
FIG. 17 is a flowchart illustrating an example of the processing performed by a learning system according to the second exemplary embodiment.

FIG. 17 is a flowchart illustrating an example of the processing performed by the learning system 1000A according to the second exemplary embodiment.

(Steps S300 to S305)

Like the learning system 1000 according to the first exemplary embodiment, the learning system 1000A performs the processes in steps S300 to S305.

(Step S306a)

Subsequently, the motivational state determination unit 104a determines the motivational state of the user by using the result of determination as to whether the first motivation is present made by the first motivation determination unit 102 (step S302) and the result of determination as to whether the second motivation is present made by the second motivation determination unit 103 (step S305). That is, according to the present exemplary embodiment, the motivational state determination unit 104a determines which of state 1, state 2, and state 3 illustrated in FIG. 15 is the motivational state of the user.

(Step S307a)

The response presentation unit 108a selects and outputs a response related to the user's motivational state on the basis of the result of determination made by the motivational state determination unit 104a. According to the present exemplary embodiment, if it is determined that the motivational state is state 3, the response presentation unit 108a selects and outputs a message prompting the user to take a break. The output response is displayed in the response presentation field 602 of the screen 600 illustrated in FIG. 11 at the time t3 at which the response is presented illustrated in FIG. 6.

(Step S308)

The problem presentation unit 107a selects and outputs a problem to be subsequently presented, which is related to the user's motivational state, on the basis of the result of determination of the user's motivation made by the motivational state determination unit 104a. For example, if it is determined that the user's motivational state is state 2, the problem presentation unit 107a selects and outputs a problem associated with a difficulty level that differs from the difficulty level associated with the problem presented in step S300. The output problem is displayed in the problem presentation field 601 of the screen 600 illustrated in FIG. 11, instead of the problem currently displayed in the question presentation field 601.

Summary of Second Exemplary Embodiment

According to the present exemplary embodiment, if a first motivation is present and a second motivation is not present, the control unit 110a instructs the output unit 106 to output the fourth problem having a difficulty level that differs from the difficulty level of the first problem. In contrast, if the second motivation is present, the control unit 110a instructs the output unit 106 to output a fifth problem having a difficulty level that is the same as the difficulty level of the first problem. Note that the first problem is the current problem, and the fourth or fifth problem is the next problem.

As described above, if a first motivation is present and a second motivation is not present, that is, if the user is in a low motivational state, the fourth problem having a difficulty level that differs from the difficulty level of the first problem is output. Thus, the probability of recovery of the motivation of the user can be increased. As a result, the learning effect can be improved. In contrast, if the second motivation is present, the user is in a state called a normal state. That is, it is highly likely that the motivation present before the presentation of the first problem continuously remains without being decreased by the content of the first problem. Alternatively, it is highly likely that motivation that was not present before the presentation of the first problem is recovered by the content of the first problem. Therefore, the difficulty level of the first problem is suitable for maintaining or recovering the motivation of the user. Accordingly, in the learning system 1000A according to the present exemplary embodiment, when the user is in the normal state, the fifth problem having a difficulty level that is the same as the difficulty level of the first problem is output. As a result, the motivation of the user in the normal state can be maintained or restored and, thus, the learning effect can be improved.

More specifically, to output a fourth problem, the control unit 110a refers to a database storing a plurality of problems each associated with one the difficulty levels of the problems and outputs a fourth problem associated with a difficulty level that is lower or higher than the difficulty level associated with the first problem. In addition, to output a fifth problem, the control unit 110a refers to the database and outputs a fifth problem associated with a difficulty level the same as the difficulty level associated with the first problem.

In this manner, the fourth problem having a difficulty level that differs from the difficulty level of the first problem can be appropriately output. In addition, the fifth problem having a difficulty level that is the same as the difficulty level of the first problem can be appropriately output.

Third Exemplary Embodiment

Unlike the second exemplary embodiment, according to the third exemplary embodiment, information as to whether the answer is correct or incorrect acquired by the acquisition unit 105 is used to select the next problem. More specifically, in the case where it is determined that a first motivation is present before a problem is presented and a second motivation is not present after the answer is input, if the user's answer is correct, a problem having a higher difficulty level is selected as the next problem. However, if the user's answer is incorrect, an easier problem to solve is selected as the next problem. That is, according to the present exemplary embodiment, if the motivation of the user decreases due to the content of the presented problem, the difficulty level of the presented problem is inappropriate and, thus, a problem having an appropriate difficulty level is presented as the next problem. In this manner, the motivation of the user can be improved and, thus, the learning effect can be improved.

System Configuration

Figure 18:
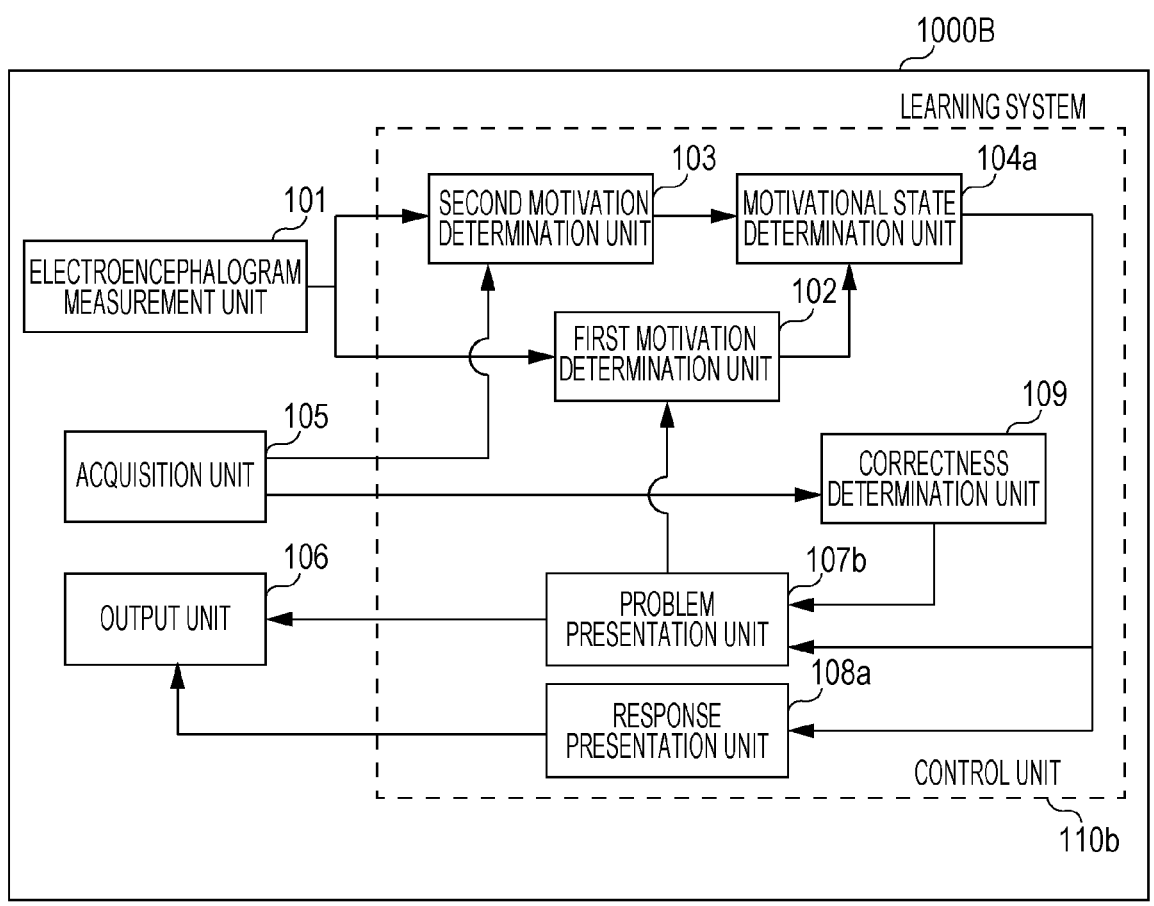
FIG. 18 illustrates an example of the functional configuration of a learning system according to a third exemplary embodiment.

FIG. 18 illustrates an example of the functional configuration of a learning system according to the present exemplary embodiment. According to the present exemplary embodiment, the same reference numerals are used to describe constituent elements that are the same as in the first or second exemplary embodiment, and detailed description of the constituent elements are not repeated.

A learning system 1000B according to the present exemplary embodiment includes a problem presentation unit 107b instead of the problem presentation unit 107a according to the second exemplary embodiment. The learning system 1000B further includes a correctness determination unit 109. Therefore, according to the present exemplary embodiment, the first motivation determination unit 102, the second motivation determination unit 103, the motivational state determination unit 104a, the problem presentation unit 107b, the response presentation unit 108a, and the correctness determination unit 109 are constituent elements included in a control unit 110b. Like the control unit 110 according to the first exemplary embodiment, the control unit 110b is configured as at least one processor, for example.

Correctness Determination Unit

The correctness determination unit 109 determines whether the answer acquired by the acquisition unit 105 is correct. More specifically, the correctness determination unit 109 refers to a database storing a plurality of problems each associated with the correct answer of the problem and determines whether the acquired answer is the correct answer. Thereafter, the correctness determination unit 109 notifies the problem presentation unit 107b of the result of determination.

Note that this database may be provided in the learning system 1000B or the terminal device 100. Alternatively, the database may be provided in a server installed outside the learning system 1000B. When a database is provided in the server, the correctness determination unit 109 refers to the database in the server via, for example, the Internet.

Problem Presentation Unit

The problem presentation unit 107b acquires the result of determination as to whether the answer is correct, which is sent from the correctness determination unit 109. The problem presentation unit 107b has a function similar to that of the problem presentation unit 107a according to the second exemplary embodiment. However, when changing the difficulty level of a problem to be subsequently presented, the problem presentation unit 107b changes the difficulty level on the basis of the result of determination of the correctness of the answer sent from the correctness determination unit 109. That is, the problem presentation unit 107b changes the difficulty level of the problem to be subsequently presented on the basis of the result of determination of the user's motivational state sent from the motivational state determination unit 104a and the result of determination of the correctness of the answer sent from the correctness determination unit 109.

More specifically, in the case where the answer acquired by the acquisition unit 105 is a correct answer, the first motivation is present, and the second motivation is not present, the problem presentation unit 107b instructs the output unit 106 to output a second problem having a difficulty level higher than the difficulty level of the first problem. The first problem is a problem corresponding to the answer acquired by the acquisition unit 105 and is a current problem. The second problem is a problem to be subsequently presented, which is more difficult than the current problem to solve. In addition, the case where the first motivation is present and the second motivation is not present occurs when the motivational state of the user is state 2, that is, the low motivational state.

More specifically, the problem presentation unit 107b refers to a database storing a plurality of problems each associated with one of the difficulty levels of the problems and instructs the output unit 106 to output a second problem associated with a difficulty level higher than the difficulty level associated with the first problem.

Note that the database may be provided in the learning system 1000B or the terminal device 100. Alternatively, the database may be provided in a server installed outside the learning system 1000B. The problem presentation unit 107b may include the database. The database may be included in the memory. When the database is provided in the server, the problem presentation unit 107b refers to the database in the server via, for example, the Internet.

However, in the case where the answer acquired by the acquisition unit 105 is incorrect, the first motivation is present, and the second motivation is not present, the problem presentation unit 107b instructs the output unit 106 to output a third problem that is easier than the first problem to solve. The third problem is a problem to be subsequently presented, which is easier than the current problem (that is, the first problem) to solve.

More specifically, the problem presentation unit 107b refers to the above-described database storing a plurality of problems each associated with one of the difficulty levels of the problems and instructs the output unit 106 to output a third problem associated with a difficulty level lower than the difficulty level associated with the first problem.

As described above, the problem presentation unit 107b uses the result of determination of the user's motivational state sent from the motivational state determination unit 104a and further uses the result of determination of the correctness of the answer sent from the correctness determination unit 109 to change the difficulty level of the subsequently presented problem.

Figure 19:
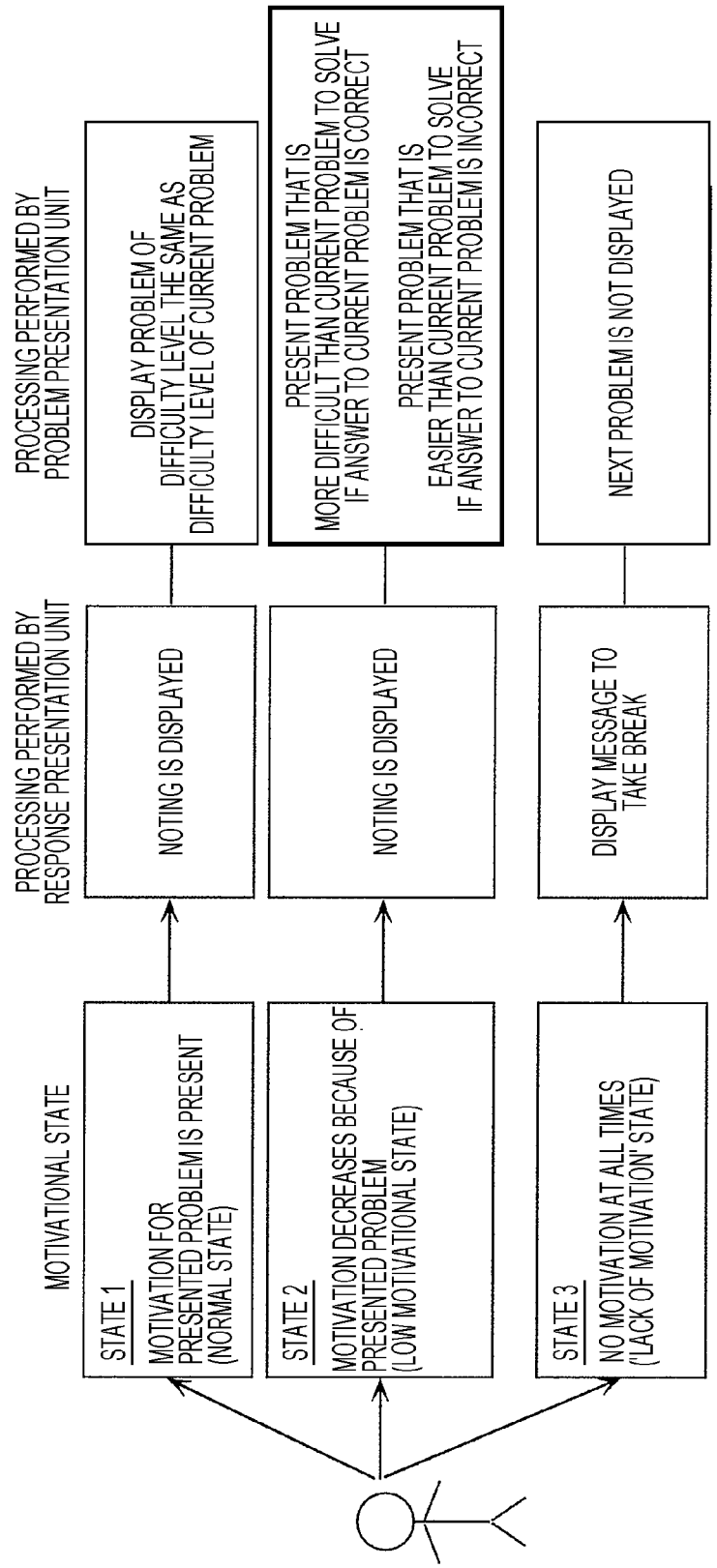
FIG. 19 illustrates the processing that corresponds to each of the motivational states and that is performed by a problem presentation unit and a response presentation unit according to the third exemplary embodiment.

Response Presentation and Problem Presentation Corresponding to Motivational State FIG. 19 illustrates the processing that corresponds to each of the motivational states and that is performed by the problem presentation unit 107b and the response presentation unit 108a according to the third exemplary embodiment.

Unlike the second exemplary embodiment, according to the present exemplary embodiment, if the motivational state of the user determined by the motivational state determination unit 104a is state 2, the problem presentation unit 107b changes the difficulty level of a problem to be subsequently presented on the basis of the result of determination made by the correctness determination unit 109. However, if the motivational state of the user determined by the motivational state determination unit 104a is state 1 or state 3, the problem presentation unit 107b performs processing that is the same as the processing performed by the problem presentation unit 107a according to the second exemplary embodiment.

More specifically, when it is determined that the user's motivational state is state 2, that is, a low motivational state, and the result of determination of the correctness determination unit 109 is a correct answer, the problem presentation unit 107b presents, as the subsequently presented problem, a problem that is more difficult to solve via the output unit 106. The difficult problem corresponds to the second problem described above. The reason for presenting a difficult problem is that it is highly likely that the motivation of the user has decreased because the current problem (corresponding to the first problem described above) was too easy to solve. However, if it is determined that the user's motivational state is state 2, that is, a low motivational state, and the result of determination made by the correctness determination unit 109 is an incorrect answer, the problem presentation unit 107b presents, as the subsequently presented problem, an easier problem to solve via the output unit 106. Note that the easier problem to solve corresponds to the third problem described above. The reason for presenting an easier problem is that it is highly likely that the user's motivation decreases because the current problem (corresponding to the first problem described above) is too difficult to solve.

Process Flow of Learning System

Figure 20:
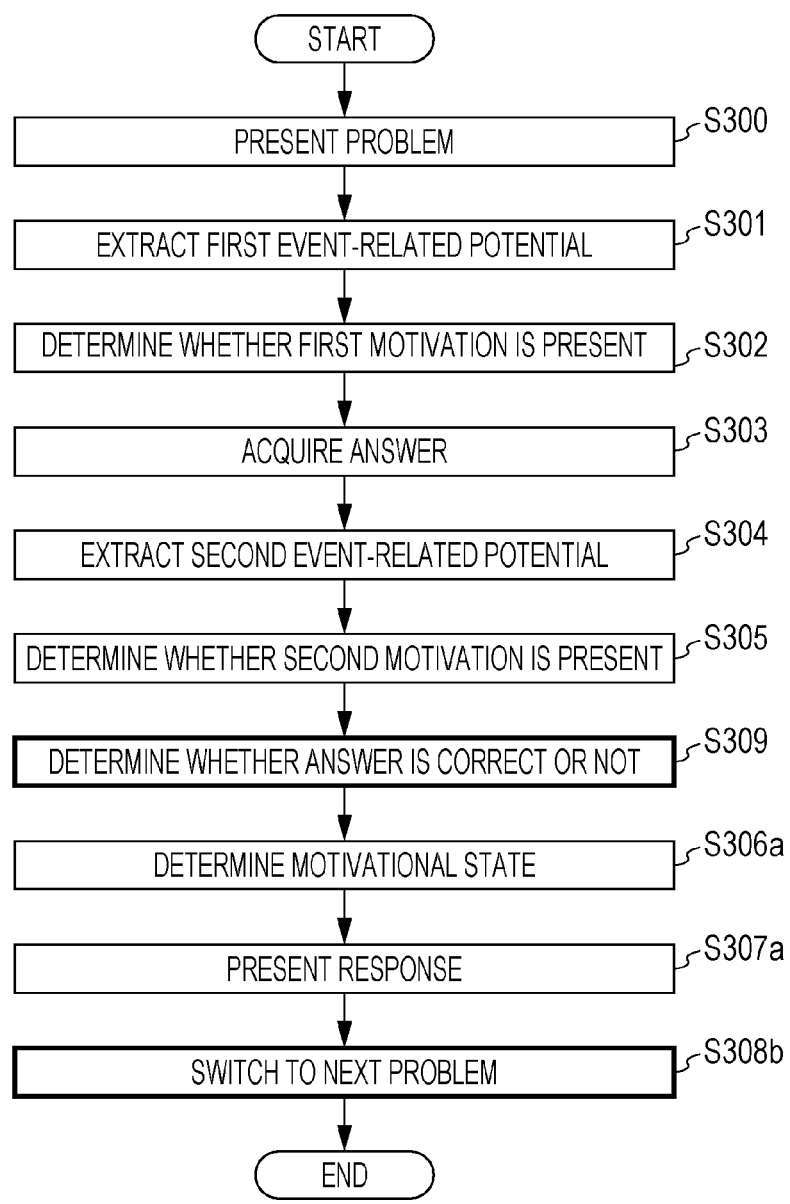
FIG. 20 is a flowchart illustrating the processing performed by the learning system according to the third exemplary embodiment.

FIG. 20 is a flowchart illustrating the processing performed by the learning system 1000B according to the present exemplary embodiment.
(Steps S300 to S305)

Like the learning system 1000 according to the first exemplary embodiment or the learning system 1000A according to the second exemplary embodiment, the learning system 1000B performs the processes in steps S300 to S305.
(Step S309)

The correctness determination unit 109 determines whether the user's answer acquired in step S303 is a correct answer.
(Step S306a)

Subsequently, the motivational state determination unit 104a determines the user's motivational state on the basis of the result of determination as to whether a first motivation is present made by the first motivation determination unit 102 (step S302) and the result of determination as to whether a second motivation is present made by the second motivation determination unit 103 (step S305). That is, according to the present exemplary embodiment, the motivational state determination unit 104a determines which of state 1, state 2, and state 3 illustrated in FIG. 15 is the user's motivational state.
(Step S307a)

The response presentation unit 108a selects and outputs a response related to the user's motivational state on the basis of the result of determination made by the motivational state determination unit 104a. According to the present exemplary embodiment, if it is determined that the motivational state is state 3, the response presentation unit 108a selects and outputs a message prompting the user to take a break. The output response is displayed in the response presentation field 602 of the screen 600 illustrated in FIG. 11 at the time t3 at which the response is presented illustrated in FIG. 6.
(Step S308b)

The problem presentation unit 107b selects and outputs a problem that is related to the user's motivational state and that is to be subsequently presented on the basis of the result of determination of the user's motivational state made by the motivational state determination unit 104a and the result of determination of the correctness of the answer made by the correctness determination unit 109. For example, if it is determined that the user's motivational state is state 2 and that the user's answer is correct, the problem presentation unit 107b selects and outputs a problem associated with the difficulty level higher than the difficulty level associated with the problem presented in step S300. However, if it is determined that the user's motivational state is state 2 and that the user's answer is incorrect, the problem presentation unit 107b selects and outputs a problem associated with the difficulty level lower than the difficulty level associated with the problem presented in step S300. The problem output in a manner described above is displayed in the problem presentation field 601 of the screen 600 illustrated in FIG. 11, instead of the currently displayed problem.

Summary of Third Exemplary Embodiment

According to the present exemplary embodiment, the control unit 110b determines whether the acquired answer is a correct answer. Thereafter, when the acquired answer is a correct answer and if the first motivation is present and the second motivation is not present, the control unit 110b instructs the output unit 106 to display a second problem that is more difficult than the first problem to solve. Note that the first problem is the current problem, and the second problem is the next problem that is more difficult than the current problem to solve.

If the first motivation is present and the second motivation is not present, the user is in a state called a low motivational state. That is, it is highly likely that the motivation present before the presentation of the first problem decreases because of the content of the first problem. The reason for the decrease in motivation is that the difficulty level of the first problem is too high or too low for the user. However, if the user's answer is correct, the cause can be limited to the first problem having a difficulty level that is too low for the user. Therefore, in the learning system 1000B according to the present exemplary embodiment, when the user is in a low motivational state and the answer is correct, a second problem that is more difficult than the first problem to solve is output. In this manner, the motivation of the user can be recovered and, thus, the learning effect can be improved.

In addition, according to the present exemplary embodiment, the control unit 110b determines whether the acquired answer is correct. Thereafter, when the acquired answer is incorrect and if first motivation is present and the second motivation is not present, the control unit 110b instructs the output unit 106 to display a third problem that is easier than the first problem to solve. Note that the first problem is the current problem, and the third problem is the next problem that is easier than the current problem to solve.

If the user is in a low motivational state and the user's answer is incorrect, the cause can be limited to the first problem having a difficulty level that is too high for the user. Therefore, in the learning system 1000B according to the present exemplary embodiment, if the user is in a low motivation state and the answer is incorrect, a third problem which is easier than the first problem to solve is output. In this manner, the motivation of the user can be recovered and, thus, the learning effect can be improved.

In addition, according to the present exemplary embodiment, to determine whether the answer is correct, the control unit 110b refers to the database storing a plurality of problems each associated with the correct answer of the problem and determines whether the acquired answer is correct. Thereafter, to output the second problem, the control unit 110b refers to the database storing a plurality of problems each associated with one of the difficulty levels of the problems and instructs the output unit 106 to output a second problem associated with a difficulty level high than the difficulty level associated with the first problem.

In this manner, it can be appropriately determined whether the answer is correct. In addition, the second problem having a difficulty higher than the difficulty level of the first problem can be appropriately output.

In addition, according to the present exemplary embodiment, to determine whether the answer is correct, the control unit 110b refers to the database storing a plurality of problems each associated with the correct answer of the problem and determines whether the acquired answer is correct. Thereafter, to output the third problem, the control unit 110b refers to the database storing a plurality of problems each associated with one of the difficulty levels of the problems and instructs the output unit 106 to output a third problem associated with a difficulty level lower than the difficulty level associated with the first problem.

Thus, it can be appropriately determined whether the answer is correct. In addition, the third problem having a difficulty level lower than the difficulty level of the first problem can be appropriately output.

As described above, according to the present exemplary embodiment, if it is determined that the user is not motivated after inputting the answer, it is determined whether motivation is not present before the problem is presented or the motivation decreased due to the content of the presented problem. If motivation is not present before the problem is presented, a message prompting the user to take a break is output. However, according to the present exemplary embodiment, if the motivation is lowered by the content of the presented problem, the information as to whether the input answer is correct is used. As a result, according to the present exemplary embodiment, if the answer is correct, the next problem is changed to a problem that is more difficult than the current problem to solve. However, if the answer is incorrect, the next problem is changed to a problem that is easier than the current problem to solve. In this way, by speculating the cause of a decrease in the user's motivation and performing control on the basis of the cause, the motivation of the user can be improved. As a result, the learning effect can be improved.

Note that in the learning control apparatus described in Japanese Unexamined Patent Application Publication No. 10-78743 or the service providing system described in Japanese Patent No. 4189440 as an existing learning system in the "Background Art" section, a method for questioning a problem is switched on the basis of the depth of user's understanding estimated from the method for inputting the answer. However, to improve the learning effect, usage of only the depth of the user's understanding is insufficient. For example, when the answer is incorrect in a situation where the user's motivation is low, the user's motivation is not improved if easier questions are repeatedly presented. In addition, since the decrease in the user's motivation is not always due to a single cause, it is necessary to speculate the cause of the decrease in the user's motivation and encourage the user in a way in accordance with the speculated cause. According to the present exemplary embodiment, the learning effect can be improved by speculating the motivational state at the time of learning and changing the feedback to the user on the basis of the result of speculation.

SUMMARY OF PRESENT DISCLOSURE

As described above, in the learning system according to an aspect of the present disclosure, if a user is in a 'lack of motivation' state, a display message prompting the user to take a break is output, so that the motivation of the user can be recovered. As a result, the learning effect can be improved.

Other Embodiments

The learning system according to each of the above-described first to third exemplary embodiments is formed from the terminal device and the electroencephalograph 200. However, the configuration of the learning system according to the present disclosure is not limited to such a configuration.

Figure 21:
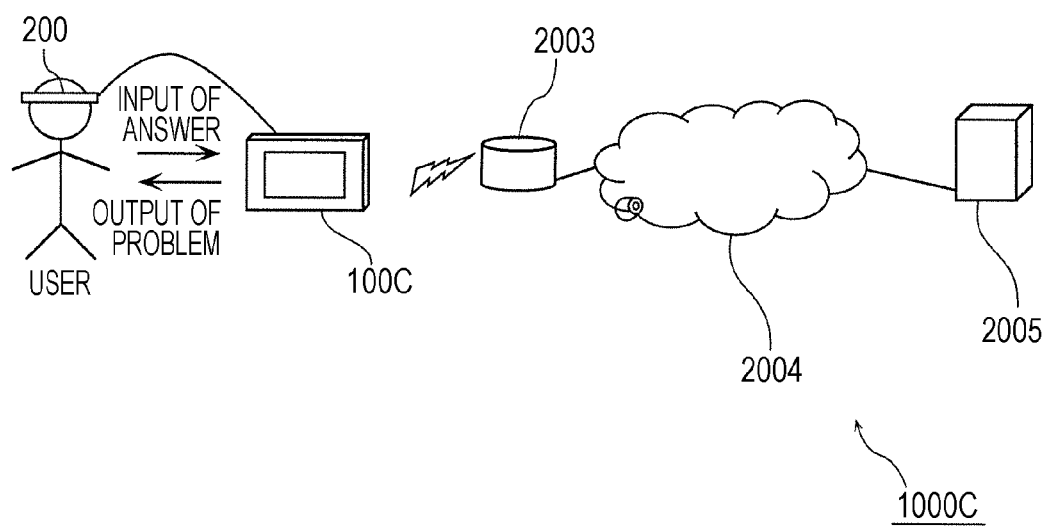
FIG. 21 illustrates another example of the external configuration of the learning system according to the present disclosure.

FIG. 21 illustrates another example of the external configuration of the learning system according to the present disclosure.

In this example, a learning system 1000C includes an electroencephalograph 200, a terminal device 100C, and a server 2005. The terminal device 100C and the server 2005 function as the terminal device 100 of each of the above-described first to third exemplary embodiments by communicating with each other via a wireless device 2003 and the Internet 2004. In such a case, the terminal device 100C may include at least one of the plurality of constituent elements of the terminal device 100, and the server 2005 may include the other constituent elements. For example, the terminal device 100C may include the acquisition unit 105 and the output unit 106, and the server 2005 may include the control unit 110, 110a or 110b. Even the learning system 1000C having such a configuration can perform the learning method similar to that of the learning system according to each of the above-described first to third exemplary embodiments.

That is, in the example illustrated in FIG. 21, the processing of the learning method is not performed by only the terminal device 100C. The terminal device 100C and the server 2005 communicate with each other via the wireless device 2003 and the Internet 2004 and perform a variety of processes included in the learning method.

In addition, according to the present disclosure, all or some of the units, devices, members, and parts or all or some of the functional blocks in the block diagram illustrated in FIGS. 4, 5, 14, and 18 may be realized by one or more electronic circuits including a semiconductor device, a semiconductor integrated circuit (IC), or a large scale integration (LSI). The LSI or IC may be integrated into one chip or may be formed by combining a plurality of chips. For example, the functional blocks other than a memory device may be integrated into one chip. Note that although the term "LSI" is used herein, the term "system LSI", "VLSI (very large scale integration)", or "ULSI (ultra large scale integration)" may be used as well depending on the level of integration. Alternatively, a field programmable gate array (FPGA), which is programmed after fabrication of the LSI, or a reconfigurable logic device, which allows reconfiguration of the connection relationship inside the LSI or setup of circuit partitions inside the LSI, may be employed for the same purpose.

In addition, some or all of the functions or the operations of the units, devices, members and parts may be performed through software processing. In such a case, the software is recorded on at least one non-transitory storage medium, such as a ROM, an optical disc, and a hard disc drive. When the software is executed by a processor, the function identified by the software is performed by the processor and peripheral devices. The system or apparatus may include one or more non-transitory recording media each having the software recorded thereon, a processor, and a required hardware device (e.g., an interface).

Furthermore, each of the control units 110, 110a and 110b in the above-described exemplary embodiments includes a processor and a memory, and the memory may store the programs for performing the steps in the flowchart illustrated in FIG. 7, 8, 12, 13, 17, or 20. In such a case, the processor executes the programs stored in the memory.

The present disclosure is applicable to a learning system using, for example, a terminal device providing a plurality of input/output operations, such as screen display and screen input. The present disclosure is effective for improving learning efficiency of a user.

What is claimed is:

1. A learning system comprising:
   an outputter that outputs a first problem to a user at a first time;
   an acquisitor that receives an answer to the first problem from the user at a second time;
   an electroencephalogram measurer that measures an electroencephalogram of the user indicating a first event-related potential during a first time window starting from the first time and ending before the second time, and a second event-related potential during a second time window starting from the second time; and
   a controller,
   wherein the controller determines whether a first motivation of the user is present on the basis of the first event-related potential during the first time window (a), determines whether a second motivation of the user is present on the basis of the second event-related potential during the second time window (b), and instructs the outputter to output a display message prompting the user to take a break if the first motivation is not present during the first time window and the second motivation is not present during the second time window (c).

2. The learning system according to claim 1, wherein in (a), the controller extracts the first event-related potential from the electroencephalogram (a1), and
   wherein in (b), the controller extracts the second event-related potential from the electroencephalogram (b1).

3. The learning system according to claim 2, wherein the first time window is a time window of 250 msec to 500 msec after the output of the first problem.

4. The learning system according to claim 2, wherein the second time window is a time window of 250 msec to 500 msec after the acquisition of the answer.

5. The learning system according to claim 1, wherein the controller further determines whether the acquired answer is correct (d), and
   wherein in the case where the acquired answer is correct, the first motivation is present, and the second motivation is not present (e1), the controller instructs the outputter to output a second problem that is more difficult than the first problem to solve (f1).

6. The learning system according to claim 1, wherein the controller further determines whether the acquired answer is correct (d), and
   wherein in the case where the acquired answer is incorrect, the first motivation is present, and the second motivation is not present (e2), the controller instructs the outputter to output a second problem that is easier than the first problem to solve (f2).

7. The learning system according to claim 5, wherein in (d), the controller refers to a database storing a plurality of problems each associated with a correct answer of the problem and determines whether the acquired answer is correct, and
   wherein in (f1), the controller refers to the database storing a plurality of problems each associated with a correct answer of the problem and instructs the outputter to output the second problem associated with a difficulty level that is higher than the difficulty level associated with the first problem.

8. The learning system according to claim 6, wherein in (d), the controller refers to a database storing a plurality of problems each associated with a correct answer of the problem and determines whether the acquired answer is correct, and
   wherein in (f2), the controller refers to the database storing a plurality of problems each associated with a correct answer of the problem and instructs the outputter to output the second problem associated with a difficulty level that is lower than the difficulty level associated with the first problem.

9. The learning system according to claim 1, wherein if the first motivation is present and the second motivation is not present (g), the controller further instructs the outputter to output a second problem having a difficulty level that differs from the difficulty level of the first problem (h), and
   wherein if the second motivation is present (i), the controller instructs the outputter to output a third problem having a difficulty level that is the same as the difficulty level of the first problem (j).

10. The learning system according to claim 9, wherein in (h), the controller refers to a database storing a plurality of problems each associated with a difficulty level of the problem and instructs the outputter to output the second problem associated with a difficulty level that is lower or higher than the difficulty level associated with the first problem, and
    wherein in (j), the controller refers to the database and instructs the outputter to output the third problem associated with a difficulty level that is the same as the difficulty level associated with the first problem.

11. The learning system according to claim 1, wherein the controller includes a processor and a memory,
    wherein the memory stores a program used to perform (a) to (c), and the processor executes the program stored in the memory.

12. A learning method for use in a learning system including at least one processor and an outputter, comprising:
    (k1) outputting a first problem to a user at a first time via the outputter by using the processor;
    (k2) receiving an answer to the first problem from the user at a second time by using the processor;
    (k3) measuring, by using the processor, electroencephalogram of the user indicating a first event-related potential during a first time window starting from the first time and ending before the second time, and a second event-related potential during a second time window starting from the second time;

(k4) determining, by using the processor, whether a first motivation of the user is present on the basis of the first event-related potential during the first time window;

(k5) determining, by using the processor, whether a second motivation of the user is present on the basis of the second event-related potential during the second time window; and (k6) instructing the outputter to output a display message prompting the user to take a break if the first motivation is not present during the first time window and the second motivation is not present during the second time window by using the processor.

13. The learning method according to claim 12, wherein in step (k4), the at least one processor extracts the first event-related potential from the electroencephalogram, and wherein in step (k5), the at least one processor extracts the second event-related potential from the electroencephalogram.

14. The learning method according to claim 13, wherein the first time window is a time window of 250 msec to 500 msec after the output of the first problem.

15. The learning method according to claim 13, wherein the second time window is in a time window of 250 msec to 500 msec after the acquisition of the answer.

16. The learning method according to claim 12, wherein the at least one processor further determines whether the acquired answer is correct (k6), and wherein in the case where the acquired answer is correct, the first motivation is present, and the second motivation is not present (k7), the at least one processor instructs the outputter to output a second problem that is more difficult than the first problem to solve (k8).

17. The learning method according to claim 12, wherein the at least one processor further determines whether the acquired answer is correct (k6), and wherein in the case where the acquired answer is incorrect, the first motivation is present, and the second motivation is not present (k9), the at least one processor instructs the outputter to output a second problem that is easier than the first problem to solve (k10).

18. The learning method according to claim 16, wherein in step (k6), the at least one processor refers to a database storing a plurality of problems each associated with a correct answer of the problem and determines whether the acquired answer is correct, and wherein in step (k8), the controller refers to a database storing a plurality of problems each associated with a correct answer of the problem and instructs the outputter to output the second problem associated with a difficulty level that is higher than the difficulty level associated with the first problem.

19. The learning method according to claim 17, wherein in step (k6), the at least one processor refers to a database storing a plurality of problems each associated with a correct answer of the problem and determines whether the acquired answer is correct, and wherein in step (k10), the at least one processor refers to a database storing a plurality of problems each associated with a correct answer of the problem and instructs the outputter to output the second problem associated with a difficulty level that is lower than the difficulty level associated with the first problem.

20. The learning method according to claim 12, wherein if the first motivation is present and the second motivation is not present (k11), the at least one processor further instructs the outputter to output a second problem having a difficulty level that differs from the difficulty level of the first problem (k12), and wherein if the second motivation is present (k13), the at least one processor instructs the outputter to output a third problem having a difficulty level that is the same as the difficulty level of the first problem (k14).

21. The learning method according to claim 20, wherein in step (k12), a database storing a plurality of problems each associated with a difficulty level of the problem is referred to, and the second problem associated with a difficulty level that is lower or higher than the difficulty level associated with the first problem is output, and wherein in step (k14), the database storing a plurality of problems each associated with a difficulty level of the problem is referred to, and the third problem associated with a difficulty level that is the same as the difficulty level associated with the first problem is output.

22. A non-transitory computer-readable storage medium storing a program used to cause an apparatus including a processor to perform a process, the process comprising:

(k1) outputting a first problem to a user at a first time via the outputter;

(k2) receiving the answer to the first problem from the user at a second time;

(k3) measuring electroencephalogram of the user indicating a first event-related potential during a first time window starting from the first time and ending before the second time, and a second event-related potential during a second time window starting from the second time;

(k4) determining whether a first motivation of the user is present on the basis of the first event-related potential during the first time window;

(k5) determining whether a second motivation of the user is present on the basis of the second event-related potential during the second time window; and (k6) instructing the outputter to output a display message prompting the user to take a break if the first motivation is not present during the first time window and the second motivations is not present during the second time window.

23. An apparatus comprising:

a memory that stores a first problem, a second problem, a third problem, first information indicating that a difficulty of the first problem is a first level, second information indicating that a difficulty of the second problem is the first level, and third information indicating that a difficulty of the third problem is a second level different from the first level;

a detector that detects an electroencephalogram of a user; and a processor that (i) causes a display to display the first problem at a first time, (ii) makes a first determination about whether a first average voltage of voltages, included in the electroencephalogram, during a time window after the first time and before a second time, is equal or bigger than a first predetermined voltage, (iii) receives a first answer to the first problem from the user via an input device at the second time, (iv) makes a second determination about whether a second average voltage of voltages, included in the electroencephalogram, during a time window after the second time and before a time when the second determination is made, is equal or bigger than a second predetermined voltage, and (v) instructs, based on the first determination and the second determination, the display to display information ata third time, wherein the information is the second problem when the second determination indicates the second average voltage is equal or bigger than the second predetermined voltage, wherein the information is the third problem when (i) the second determination indicates the second average voltage is smaller than the second predetermined voltage and (ii) the first determination indicates the first average voltage is equal or bigger than the first predetermined voltage, and wherein the information is a predetermined message not containing any problems including the first problem and the second problem when (i) the second determination indicates the second average voltage is smaller than the second predetermined voltage and (ii) the first determination indicates the first average voltage is smaller than the first predetermined voltage.

* * * * *